(12) United States Patent
Lukin et al.

(10) Patent No.: US 10,779,831 B2
(45) Date of Patent: Sep. 22, 2020

(54) SYSTEMS, DEVICES, AND METHODS FOR FORMING ANASTOMOSES

(71) Applicant: GI Windows, Inc., West Bridgewater, MA (US)

(72) Inventors: Peter Lukin, Norfolk, MA (US); Robert F. Beisel, Robesonia, PA (US); Christopher Thompson, Needham, MA (US); Marvin Ryou, Melrose, MA (US); James Wright, West Bridgewater, MA (US)

(73) Assignee: G.I. WINDOWS, INC., West Bridgewater, MA (US)

( * ) Notice: Subject to any disclaimer, the term of this patent is extended or adjusted under 35 U.S.C. 154(b) by 353 days.

(21) Appl. No.: 15/150,397

(22) Filed: May 9, 2016

(65) Prior Publication Data
US 2016/0324523 A1    Nov. 10, 2016

Related U.S. Application Data

(60) Provisional application No. 62/158,981, filed on May 8, 2015.

(51) Int. Cl.
*A61B 17/11* (2006.01)
*A61B 50/30* (2016.01)
(Continued)

(52) U.S. Cl.
CPC .......... *A61B 17/1114* (2013.01); *A61B 50/30* (2016.02); *A61B 1/018* (2013.01);
(Continued)

(58) Field of Classification Search
CPC . A61B 1/018; A61B 17/0218; A61B 17/1114; A61B 50/30; A61B 2017/0034;
(Continued)

(56) References Cited

U.S. PATENT DOCUMENTS

| 4,197,840 A | 4/1980 | Beck et al. |
| 4,538,130 A | 8/1985 | Gluckstern et al. |

(Continued)

FOREIGN PATENT DOCUMENTS

| DE | 3011742 A1 | 10/1981 |
| EP | 1894514 A2 | 3/2008 |

(Continued)

OTHER PUBLICATIONS

International Search Report for PCT/US2013/041641 dated Oct. 18, 2013, 4 pages.
(Continued)

*Primary Examiner* — Jocelin C Tanner
(74) *Attorney, Agent, or Firm* — Nutter McClennen & Fish LLP

(57) ABSTRACT

The invention relates to deployable magnetic compression devices and systems and methods for the deployment of such magnetic compression devices. The magnetic compression devices are particularly useful for creating anastomoses, e.g., in the gastrointestinal tract. The devices are especially useful for minimally-invasive delivery, e.g., using endoscopic techniques. The systems, devices, and methods can be used to treat a variety of gastrointestinal and metabolic diseases, such as diabetes, obesity, and cancer.

4 Claims, 38 Drawing Sheets

(51) Int. Cl.
  *A61B 17/00* (2006.01)
  *A61B 17/04* (2006.01)
  *A61B 17/02* (2006.01)
  *A61B 50/00* (2016.01)
  *A61B 1/018* (2006.01)
  *A61B 90/00* (2016.01)

(52) U.S. Cl.
  CPC ... *A61B 17/0218* (2013.01); *A61B 2017/0034* (2013.01); *A61B 2017/00362* (2013.01); *A61B 2017/00477* (2013.01); *A61B 2017/00876* (2013.01); *A61B 2017/0417* (2013.01); *A61B 2017/0461* (2013.01); *A61B 2017/0464* (2013.01); *A61B 2017/1117* (2013.01); *A61B 2017/1139* (2013.01); *A61B 2050/0072* (2016.02); *A61B 2050/3013* (2016.02); *A61B 2090/397* (2016.02); *A61B 2090/3966* (2016.02)

(58) Field of Classification Search
  CPC .......... A61B 2017/00362; A61B 2017/00477; A61B 2017/00876; A61B 2017/0417; A61B 2017/0461; A61B 2017/0464; A61B 2017/1117; A61B 2017/1139; A61B 2050/3013; A61B 2090/3966; A61B 2090/397
  See application file for complete search history.

(56) References Cited

U.S. PATENT DOCUMENTS

| | | | |
|---|---|---|---|
| 5,300,910 A | 4/1994 | Unkelbach et al. | |
| 5,595,562 A | 1/1997 | Grier | |
| 5,690,656 A | 11/1997 | Cope et al. | |
| 6,129,668 A | 10/2000 | Haynor et al. | |
| 6,132,458 A * | 10/2000 | Staehle | A61F 2/0095 623/1.11 |
| 6,190,303 B1 * | 2/2001 | Glenn | G21F 5/018 600/1 |
| 6,273,895 B1 * | 8/2001 | Pinchuk | A61B 5/1076 606/108 |
| 6,352,543 B1 | 3/2002 | Cole | |
| 6,652,540 B1 | 11/2003 | Cole et al. | |
| 6,719,768 B1 | 4/2004 | Cole et al. | |
| 6,932,827 B2 | 8/2005 | Cole | |
| 7,760,059 B2 | 7/2010 | Higuchi | |
| 8,118,821 B2 | 2/2012 | Mouw | |
| 8,142,454 B2 | 3/2012 | Harrison et al. | |
| 8,262,680 B2 | 9/2012 | Swain et al. | |
| 8,439,915 B2 | 5/2013 | Harrison et al. | |
| 8,623,036 B2 | 1/2014 | Harrison et al. | |
| 8,864,781 B2 | 10/2014 | Surti et al. | |
| 2002/0143347 A1 | 10/2002 | Cole et al. | |
| 2003/0149422 A1 * | 8/2003 | Muller | A61M 25/0136 604/528 |
| 2005/0209581 A1 * | 9/2005 | Butts | A61M 25/0097 604/523 |
| 2005/0283235 A1 | 12/2005 | Kugler et al. | |
| 2008/0051626 A1 | 2/2008 | Sato et al. | |
| 2008/0086192 A1 * | 4/2008 | Wasdyke | A61F 2/0095 623/1.12 |
| 2008/0183272 A1 * | 7/2008 | Wood | A61F 2/95 623/1.11 |
| 2008/0200934 A1 | 8/2008 | Fox | |
| 2008/0208105 A1 * | 8/2008 | Zelickson | A61B 18/22 604/20 |
| 2008/0262523 A1 | 10/2008 | Makower et al. | |
| 2009/0125042 A1 | 5/2009 | Mouw | |
| 2010/0099947 A1 | 4/2010 | Sato et al. | |
| 2011/0144560 A1 | 6/2011 | Gagner et al. | |
| 2011/0295285 A1 | 12/2011 | McWeeney et al. | |
| 2012/0022572 A1 * | 1/2012 | Braun | A61B 17/12022 606/194 |
| 2012/0197062 A1 | 8/2012 | Requarth | |
| 2012/0259350 A1 | 10/2012 | Gagner et al. | |
| 2012/0330330 A1 | 12/2012 | Gagner et al. | |
| 2013/0025355 A1 | 9/2013 | Beisel et al. | |
| 2013/0253550 A1 | 9/2013 | Beisel et al. | |
| 2014/0066709 A1 * | 3/2014 | Mirza | A61B 17/32002 600/106 |
| 2014/0018824 A1 | 7/2014 | Aronson et al. | |
| 2014/0019468 A1 | 7/2014 | Carrillo, Jr. et al. | |
| 2014/0303657 A1 * | 10/2014 | Kim | A61B 17/11 606/155 |
| 2014/0379065 A1 * | 12/2014 | Johnson | A61F 2/958 623/1.11 |

FOREIGN PATENT DOCUMENTS

| | | |
|---|---|---|
| JP | 2006271832 A | 10/2006 |
| RU | 2 018 266 C1 | 8/1994 |
| SU | 1708313 A1 | 1/1992 |
| SU | 1 725 851 A1 | 4/1992 |
| WO | 01/087398 A2 | 11/2001 |
| WO | 01/93920 A2 | 12/2001 |
| WO | 2009048954 A1 | 4/2009 |
| WO | 2011085006 A2 | 7/2011 |
| WO | 2013009886 A1 | 1/2013 |

OTHER PUBLICATIONS

International Search Report for International application No. PCT/US2011/020229, with a date of mailing of the International search report dated Jun. 21, 2013, 6 pages.

Partial and Extended European Search Report for 13793804.9 dated May 17, 2013.

Search Report and Written Opinion issued for PCT/US2015/041498 dated Nov. 17, 2015.

Search Report and Written Opinion issued for PCT/US2016/031547 dated Oct. 18, 2016.

* cited by examiner

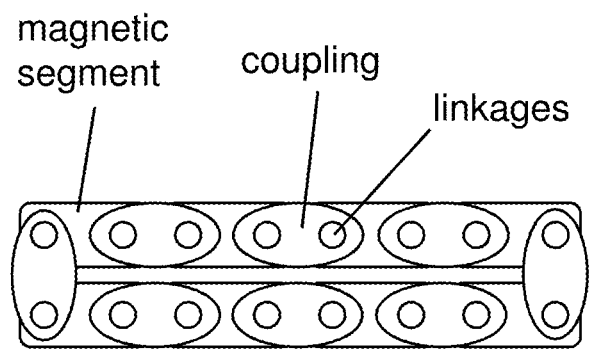
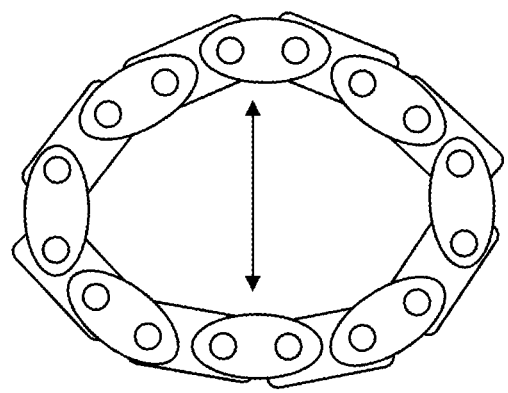
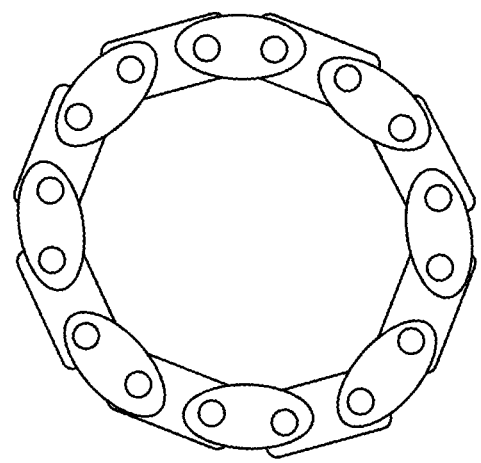
FIG. 2

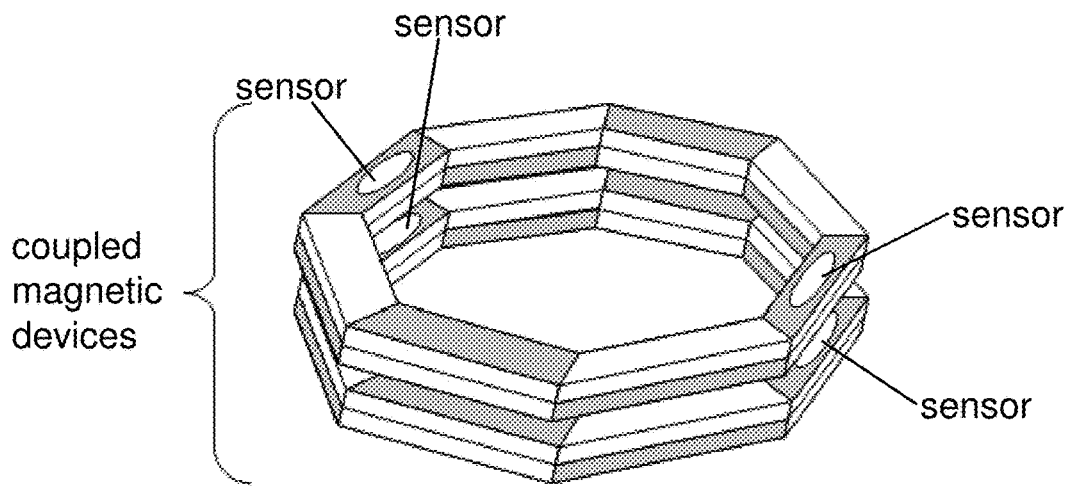
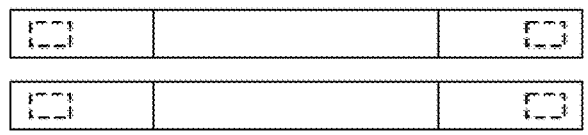
<<yes>>
Side View
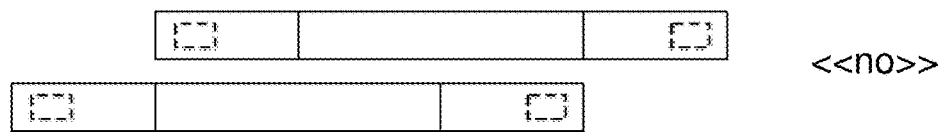
<<no>>
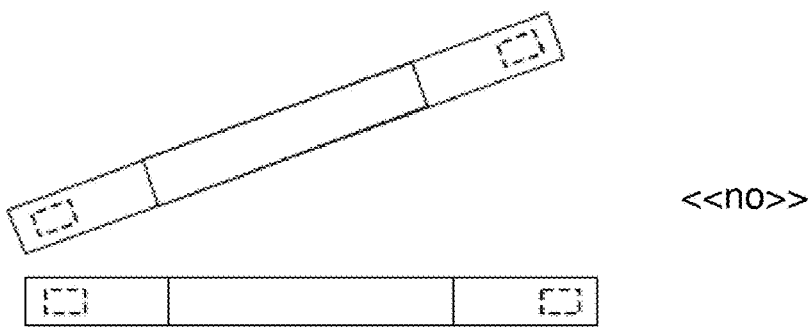
<<no>>
FIG. 15

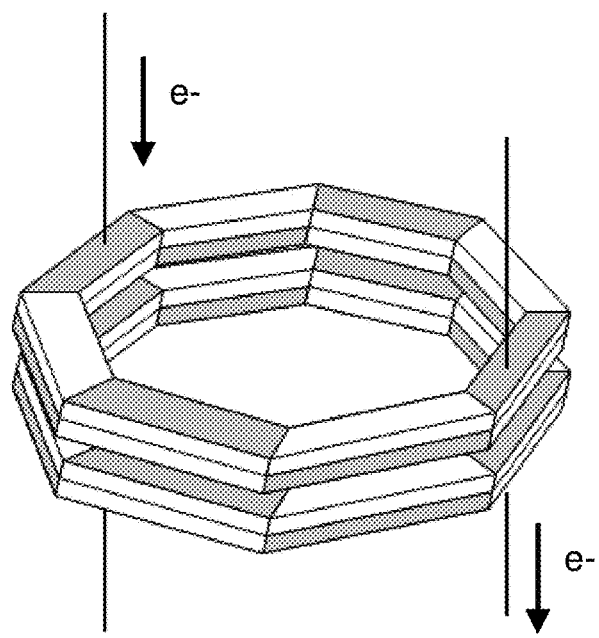
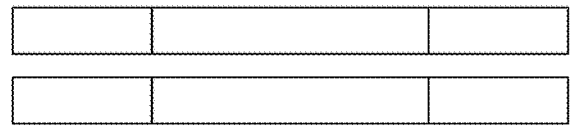
<<yes>>
Side View
<<no>>
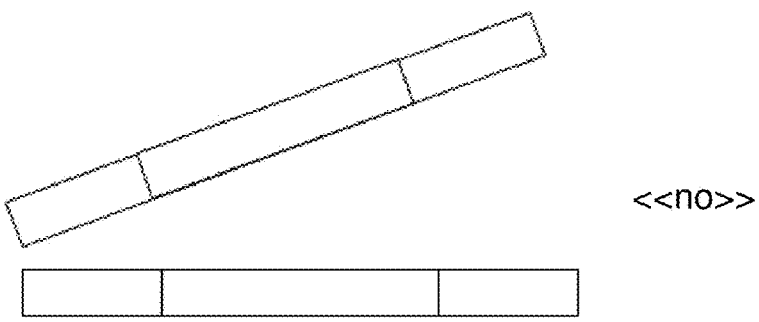
<<no>>
FIG. 16

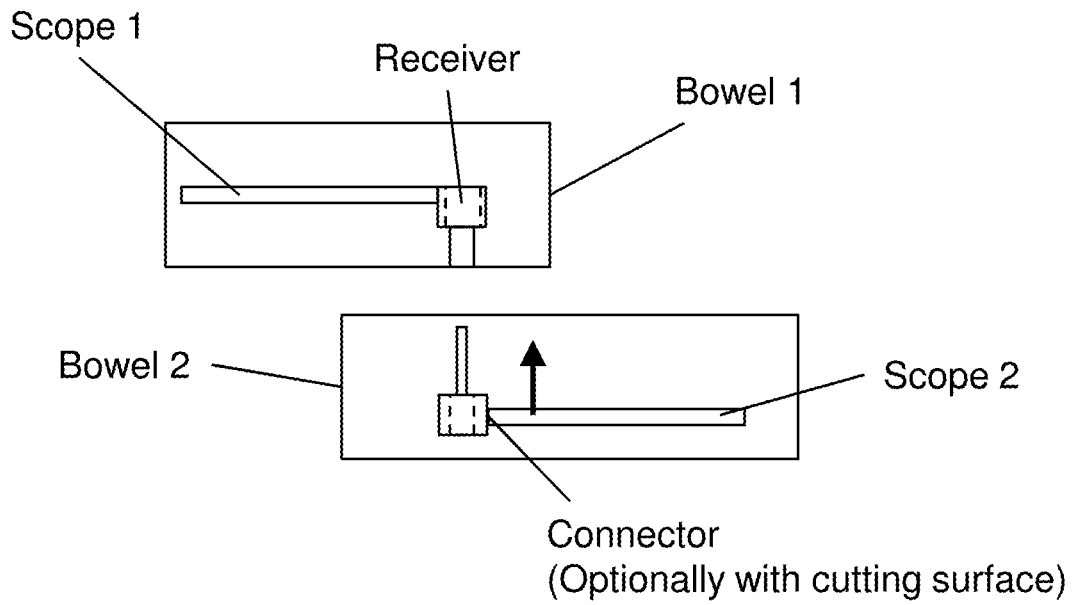
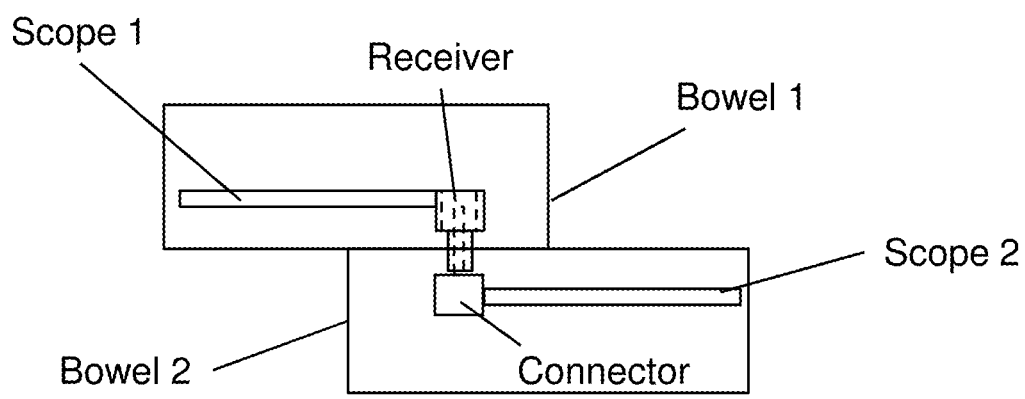
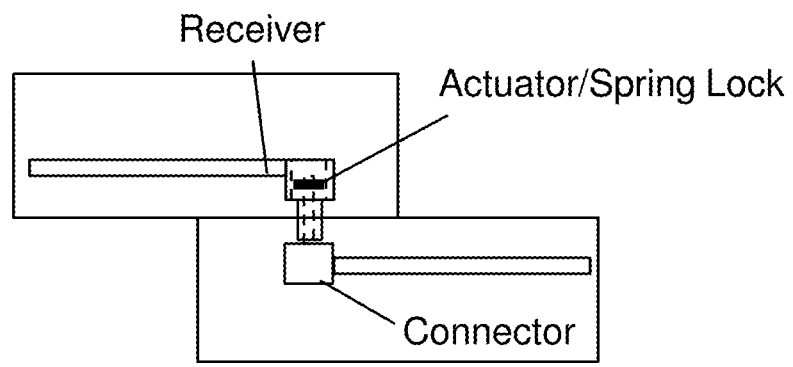
FIG. 21

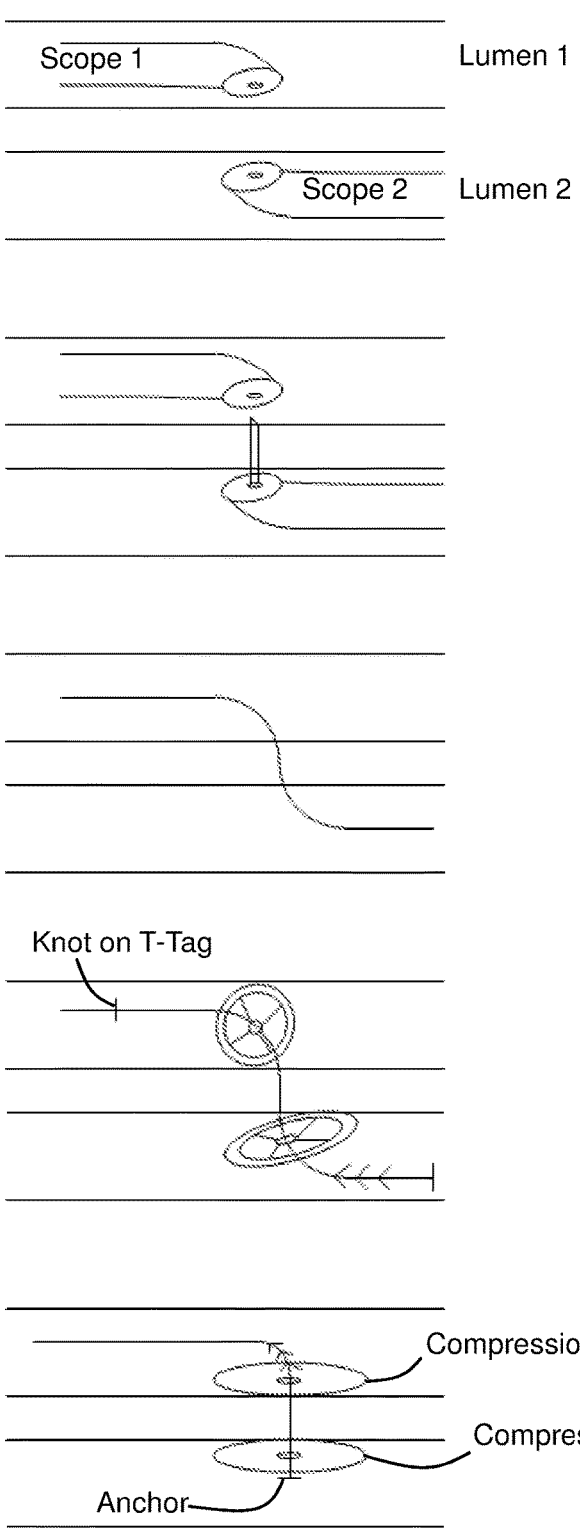

Wire-Assisted Non-Magnetic Compression Anastomosis

- Fluoroscopy and/or endoscopic light detection to confirm proximity of scope

- Transparent cap for one or both scopes to allow for sufficient visualization while scopes align

- Needle puncture by scope 2 into lumen 1

- Wire passage, capture by scope 1; wire passes into both lumens

- Withdrawal of needle

- One end of wire has "teeth" to serve as ratchets, similar to an "auto-locking" feature. An anchor is positioned at a terminal end of the wire.

- Compression device (non-magnetic) can be delivered

FIG. 28

SYSTEMS, DEVICES, AND METHODS FOR FORMING ANASTOMOSES

CROSS-REFERENCE TO RELATED APPLICATIONS

This application claims the benefit of, and priority to, U.S. Provisional Application Ser. No. 62/158,981, filed May 8, 2015, the content of which is hereby incorporated by reference herein in its entirety.

FIELD OF THE INVENTION

The invention relates to deployable magnetic compression devices and systems and methods for the deployment of the magnetic compression devices.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency.

An additional difficulty arises in that a surgeon typically cannot control the amount of magnetic attraction between deployable magnetic structures used to create an anastomosis. In some instances, it is beneficial for the magnetic devices to couple strongly at distances over 1 cm, however, in other instances, it is beneficial if the devices couple weakly at over 1 cm, and then lock together at a smaller distances. When the magnetic force is stronger than needed for a procedure, the devices may "jump" or spontaneously move together before the surgeon is ready for the devices to couple and may inadvertently trap tissues that are not intended to be joined.

Thus, there still remains a clinical need for reliable devices and minimally-invasive procedures that facilitate compression anastomosis formation between tissues in the human body.

SUMMARY

The invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The invention provides multiple configurations of magnetic devices comprising an assembly of magnetic segments that can be used to create anastomoses in a subject. Some of the devices are self-opening and designed to be delivered via a trocar using laparoscopic techniques. The self-opening devices are constructed from elongated magnetic segments and typically include hinges at first and second ends of the device, and polygon-opening members that direct the elongated magnetic segments to open upon deployment. Other configurations are self-closing, and designed to be delivered via the working channel of an endoscope. The self-closing devices typically are constructed from elongated magnetic segments coupled together in a linear arrangement by polygon-closing members that direct the device to close, and form a polygon upon deployment.

In one aspect, the present invention provides a self-closing compression anastomosis device including an assembly of magnetic segments coupled end-to-end and configured to transition between a delivery configuration, in which the magnetic segments are aligned end-to-end in a single-file arrangement defining a linear assembly having first and second ends, and a deployed configuration, in which the linear assembly forms a polygon by joining of the first and second ends. Each of the magnetic segments is configured to be coupled to a guide member, the assembly of magnetic segments is configured to translate along a length of the guide member when transitioning from the delivery configuration to the deployed configuration. When in the delivery configuration, the assembly of magnetic segments is sized to fit within a working channel of an access device and to be delivered to an anatomical structure within a patient. The access device may include, but is not limited to, an endoscope, a laparoscope, a trocar, and a cannula.

In some embodiments, at least one of the magnetic segments comprises a lumen configured to receive the guide member therethrough. The guide member may be configured to facilitate manipulation and placement of the compression anastomosis device when in the deployed configuration. The compression anastomosis device is adapted to be placed in a desired location by an elongated manipulator coupled to a portion of the guide member. The guide member may include a suture or wire. The wire may include stainless steel or nitinol material. The wire may include, for example a shape-memory alloy, such as a thermally-programmed material configured to assume a predefined shape when exposed to a target temperature. In some embodiments, the target temperature is human body temperature.

In some embodiments, the guide member includes a guidewire and the assembly is configured such that removal of the guidewire from the lumen of the at least one magnetic segment facilitates transitioning of the assembly from the delivery configuration to the deployed configuration. For example, the guidewire is configured to prevent self-assembly of the magnetic segments into the polygon while positioned within the lumen of the at least one magnetic segments and the assembly spontaneously converts from the delivery configuration to the deployed configuration once the guidewire is removed from the lumen of the at least one magnetic segment.

In some embodiments, the lumen of the at least one magnetic segment has a defined cross-sectional shape corresponding to a shape of the guide member so as to limit rotational movement of the associated magnetic segment during translation of the magnetic segment along a length of the guide member. The lumen may include a non-circular cross-sectional shape, for example. The guide member may include a cross-sectional shape corresponding to the cross-sectional shape of the lumen of the at least one magnetic segment.

In another aspect, the present invention provides a self-opening compression anastomosis device including an assembly of at least four magnetic segments coupled end-to-end to form a polygon having an out-of-plane axis, wherein each magnetic segment has a north magnetic pole and a south magnetic pole. The assembly includes a first pair of magnetic segments coupled together with a first connection member and a second pair of magnetic segments coupled together with a second connection member. The assembly includes a delivery configuration in which the magnetic segments are aligned in two rows, the two rows being joined by the first and second connection members or one or more additional connection members coupling the first and second pairs of magnetic segments to one another, and a deployed configuration in which the magnetic segments form an open polygon based, at least in part, on a force provided by at least one of the first and second connection members or the additional connection members. At least one of the magnetic segments includes a guide element configured to receive a guide member therethrough, such that the assembly of magnetic segments is configured to translate along a length of the guide member when transitioning from the delivery configuration to the deployed configuration.

In some embodiments, the guide element is a loop or sleeve having a lumen for receiving the guide member therethrough so as to allow the assembly to translate along the guide member. In some embodiments, the lumen of the loop or sleeve has a defined cross-sectional shape corresponding to a shape of the guide member so as to limit rotational movement of the associated magnetic segment during translation of the magnetic segment along a length of the guide member. For example, the lumen may include has a non-circular cross-sectional shape. Accordingly, the guide member may include a cross-sectional shape corresponding to the cross-sectional shape of the lumen of the loop or sleeve.

In some embodiments, when in the delivery configuration, the assembly of magnetic segments is sized to fit within a channel of a retaining member or sleeve configured to maintain the assembly in the delivery configuration until desired delivery of the assembly to an anatomical structure within a patient. Upon separation of the assembly from the channel of the retaining member or sleeve, the assembly is configured to spontaneously convert from the delivery configuration to the deployed configuration. When transitioning from the delivery configuration to the deployed configuration, the assembly is configured to translate along a length of the guide member. The guide member is configured to facilitate manipulation and placement of the compression anastomosis device when in the deployed configuration. The retaining member or sleeve is configured to fit within a working channel of an access device and to be delivered to an anatomical structure within a patient. The access device may include, but is not limited to endoscope, a laparoscope, a trocar, and a cannula.

In addition to providing multiple configurations of self-opening and self-closing compression anastomosis devices, the present invention provides a storage and delivery system for the storage and delivery of such compression anastomosis devices for forming an anastomosis. In particular, the present invention provides a storage and loading device configured to facilitate storage of a compression anastomosis device in a delivery configuration and further loading of the compression anastomosis member into an access device while the compression anastomosis member remains in the delivery configuration. The storage and loading device of the present disclosure overcomes current challenges that an operator may face when attempting to load a compression anastomosis device into the working channel of the access device. In particular, it may be somewhat cumbersome and difficult to maintain the compression anastomosis device in the substantially linear shape of the delivery configuration when loading into the working channel of the access device by hand. The storage and loading device is particularly advantageous in that it allows for pre-loading of the compression anastomosis device while maintained in its delivery configuration. Thus, when the operator (e.g., surgeon) is ready to deliver the anastomosis compression device to the target site, the operator need only couple the storage and loading device to a port of a working channel of an access device (e.g., scope or the like) and move the compression anastomosis device from the storage and loading device into the working channel of the access device.

In one aspect, the storage and loading device includes an elongate body having an open proximal end and an open distal end and a lumen extending between the proximal and distal ends, wherein the lumen is configured to receive a compression anastomosis device within and maintain the compression anastomosis device in a delivery configuration. The distal end of the elongate body is configured to be releasably coupled to a working channel of an access device to thereby place the lumen in fluid communication with the working channel and further align the lumen with the working channel to allow the compression anastomosis device to move from the lumen into the working channel, while remaining in the delivery configuration, for subsequent delivery from the working channel of the access device to an anatomical structure within a patient in which the compression anastomosis device transitions to a deployed configuration.

In some embodiments, the storage and loading device further includes proximal and distal cover members removably couplable to the proximal and distal ends and configured to enclose the proximal and distal ends, respectively. The proximal cover member may include a body having an aperture extending therethrough and a plug member configured to be received within and fill the aperture so as to close the proximal end from the surrounding environment. The proximal cover member may be coupled to the proximal end of the storage and loading device, wherein the aperture is in general alignment and in fluid communication with the lumen of the storage and loading device. The aperture may be configured to receive and allow an elongate manipulator to pass therethrough and into the lumen of the storage and loading device. The elongate manipulator may be configured to interact with and assist in movement of the compression anastomosis device from the lumen into the working channel of the access device.

In some embodiments, an inner surface of the aperture is configured to provide a friction fit with the external surface of the elongate manipulator. The friction fit may be sufficient to minimize an amount of gas or fluid from escaping through the lumen during movement of the compression anastomosis device into the working channel of the access device.

In some embodiments, the elongate body has an arcuate shape along a length of the body from the proximal end to the distal end and the lumen has a corresponding arcuate shape.

In some embodiments, the elongate body may include a flange extending from a portion thereof. The flange may include a contour configured to receive one or more fingers of an operator of the storage and loading device to assist in a procedure using the storage and loading device. In some embodiments, the elongate body is of a two-piece construction.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIG. 2 depicts an embodiment of a self-opening magnetic device for use to form an anastomosis;

FIG. 15 depicts magnetic devices having sensors that allow a user to determine alignment and camber of the two devices during deployment. In an embodiment, the sensors may be RFID proximity sensors built into the deployable devices;

FIG. 16 depicts magnetic devices using inductive coupling between loops of wire to allow a user to determine alignment and camber of the two devices during deployment. In an embodiment, the wires are coupled to the sides of the device so that they do not interfere with coupling of the devices;

FIG. 21 depicts an alternative embodiment for forming a magnetic anastomosis by delivering coupling devices to two different portions of bowel. Once the connector is inserted into the receiver, the components are locked together;

FIG. 28 depicts a method for creating an anastomosis between tissue by inserting a guide wire though a needle puncture and then delivering mating compression devices over the guide wire;

Figure 1:
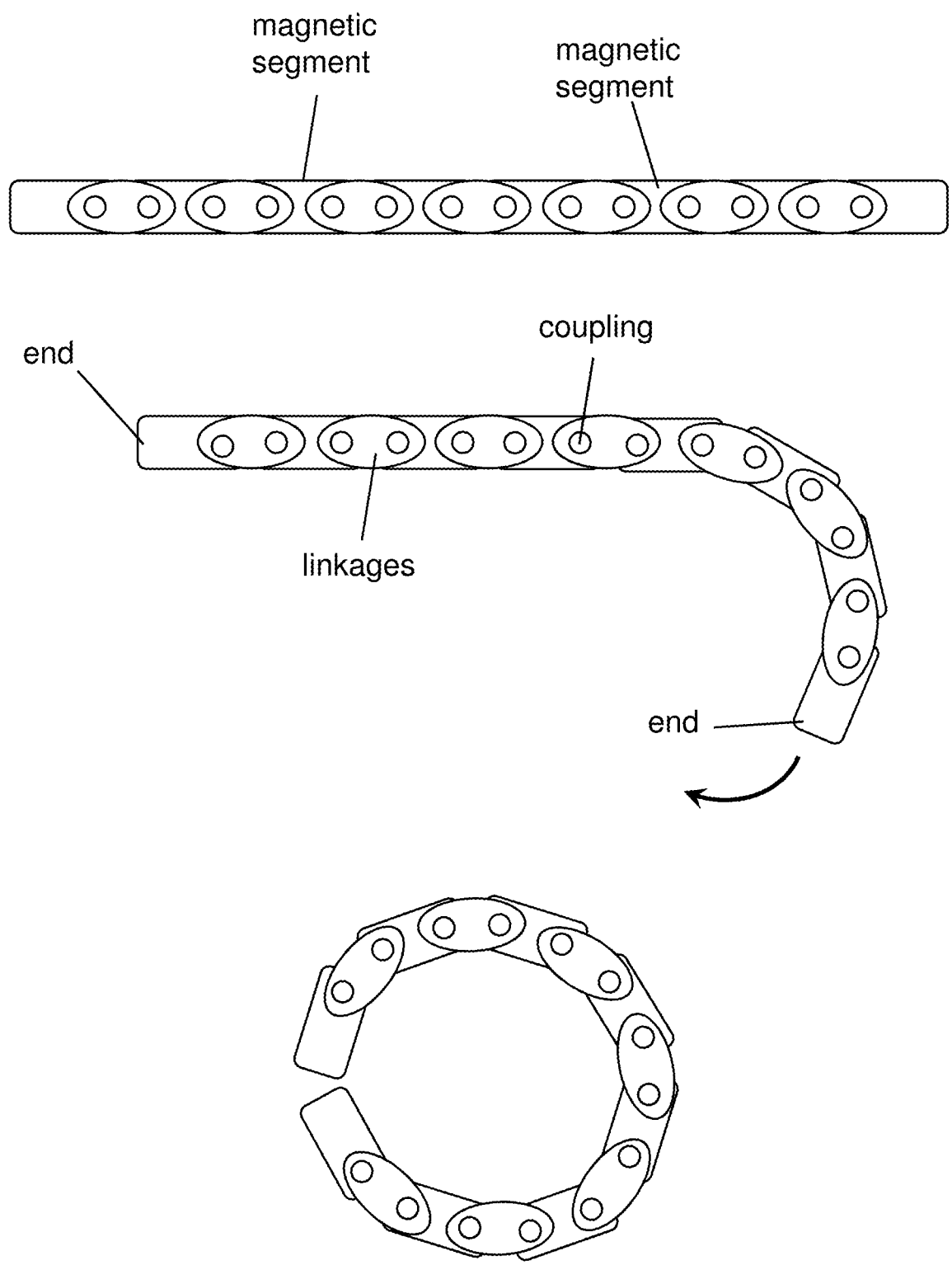
FIG. 1 depicts an embodiment of a self-closing magnetic device for use to form an anastomosis.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The invention provides multiple configurations of magnetic devices comprising an assembly of magnetic segments that can be used to create anastomoses in a subject. Some of the devices are self-opening and designed to be delivered via a trocar using laparoscopic techniques. The self-opening devices are constructed from elongated magnetic segments and typically include hinges at first and second ends of the device, and polygon-opening members that direct the elongated magnetic segments to open upon deployment. Other configurations are self-closing, and designed to be delivered via the working channel of an endoscope. The self-closing devices typically are constructed from elongated magnetic segments coupled together in a linear arrangement by polygon-closing members that direct the device to close, and form a polygon upon deployment.

The invention includes self-opening and self-closing polygonal magnetic devices that couple to each other with substantial compressive magnetic force. The invention makes it possible to create surgical anastomoses in tissue quickly with minimally-invasive techniques such as endoscopy and laparoscopy. Once the devices have are placed and mated, the compressive forces cause the vasculature of the tissue to collapse and fluids to extrude from the tissues, reducing the distance between the devices and increasing the magnetic attraction. With time, the coupled devices eventually mate completely, form an opening, and fall away from the tissue, leaving an anastomosis. The magnetic devices can, thus, be used to create surgical-quality anastomosis without the need to create an open surgical field.

With the described technique it is simpler to create openings between tissues that traditionally required open surgery or the use of complicated cutting and suturing devices. Most procedures are reduced to simply delivering a first magnetic compression device to a first tissue and then delivering a second magnetic compression device to a second tissue, and then bringing the two devices together. For example, it is straightforward to create a gastric bypass by delivering first and second magnetic devices, in the form of octagons, to the stomach and the small intestine. The magnetic force of the two devices eventually creates an anastomosis that leads from the stomach to the small intestine, reducing the working volume of the stomach.

The devices of the invention generally comprise elongated magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention.

The design of the devices can be customized depending upon the surgical techniques that will be used and the specific needs of the patient. The design specifications may include: required capture range, desired effective inner and outer diameters of the magnetic device (e.g., as defined by the desired anastomosis size and instrument passage), thickness of the target tissue, and the inner diameter of the guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument. Additionally, as described below, the arrangements of the elongated magnetic segments that make up the device may be altered to customize the amount of force between the devices 10 and 20 at a distance, e.g., at 1 cm or further apart.

Using the techniques outlined above, it is possible to create anastomoses between a variety of tissues and organs in the gastrointestinal tract. For example, anastomoses may be formed between the stomach, small intestine, gall bladder, and colon. Such techniques can be used for management of disease, such as obesity and diabetes, or such techniques can be used to improve function in the wake of disease, such as cancer. Such techniques can also be used for repair, for example, to connect portions of healthy colon after a portion of diseased colon has been removed. Such procedures can be accomplished endoscopically, laparoscopically, with an open surgical field, or with some combination of these techniques.

A device of the invention, generally, includes a plurality of elongated magnetic segments that assume the shape of a polygon once deployed in a patient. The magnetic segments are typically formed from rare earth magnets. The magnetic segments may be mitered. The magnetic segments may be coated with gold or plastic to improve their performance. In some instances, the magnets are coated with a biocompatible material. In some embodiments, the magnets are coated with a biodegradable or bioabsorbable material.

In a similar fashion, devices of differing numbers of segments, i.e., squares, hexagons, octagons, decagons, dodecagons, tetradecagons, hexadecagons, octodecagons, and icosagons can be tuned by selecting particular arrangements of magnetic poles. There are also additional reasons that a particular configuration of magnetic poles may be chosen, for example, to cause the devices to overlap correctly, or to cause the devices to connect in a way that insures that the devices cannot revert to their delivery configuration. See e.g., US 2013/0253550, incorporated herein by reference in its entirety.

In some embodiments of the invention, the deployable magnetic device is self-opening. Each device comprises a number of elongated magnetic segments, wherein two pairs of elongated magnetic segments are linked together at each end with a hinge. The magnetic segments between the hinges are linked together with polygon-opening members that direct the device to self-convert from a delivery to a deployed configuration. While the polygon-opening members are coupled to the exterior of the magnetic segments, the polygon-opening members may also be coupled to the interior of the magnetic segments. In some instances, the polygon-opening members form an exoskeleton over the magnetic segments. The polygon-opening members may be bonded or fastened to the magnetic segments or the polygon-opening members can crimp or grab the magnetic segments.

While each self-opening device comprises two hinges, the number of polygon-opening members depends upon the total number of magnetic segments in the device. For example, for a device that takes the configuration of a square upon deployment, the device will comprise four elongated magnetic segment, two hinges, and two polygon-opening members. An octagonal self-opening device may include eight elongated magnetic segments, two hinges, and six polygon-opening members. In alternate embodiments, a singular polygon opening member may span two or more elongated magnetic segments. In alternative embodiments, a quadrupolar magnetic segment can be used at the hinge end to improve opening. Quadrupolar segments are not limited to octagonal configurations, and can be used with any of the configurations described herein. Thus, it is possible to construct a self-opening octagonal device with eight magnetic segments, two hinges, and two polygon-opening members. Using the same techniques it is possible to construct deployable self-opening devices having different numbers of elongated magnetic segments that deploy as, e.g., squares, hexagons, decagons, dodecagons, tetradecagons, hexadecagons, octodecagons, or icosagons.

The self-opening devices of the invention can incorporate a variety of magnetic polar configurations. However, because of the devices need to self-convert between a side-by-side arrangement and an open polygon, it is beneficial to place the hinges such that similarly-aligned magnetic poles are next to each other in the delivery configuration. For example, each segment in the delivery configuration is next to a segment of the same magnetic orientation so that, upon delivery, the magnetic repulsions between segments drives the device into the open (deployed) configuration. In such a configuration, the primary role of the polygon-opening member is to insure that the device opens in the plane of the polygon; i.e., that out-of-plane motion of the magnetic segments is limited. The hinges of the self-opening devices may be constructed from metal (stainless steel, nickel, or nitinol) or plastic, and the hinges may be passive or active, i.e., configured to provide an opening force. In some instances, the hinges are springs. The polygon-opening members may be constructed from constructed from metal (stainless steel, nickel, or nitinol) or plastic. The polygon opening members are typically active in that they provide a force to drive the device from a delivery configuration to a deployment configuration. In some embodiments, the polygon opening members are constructed from a bioabsorbable material that facilitates separation of the magnetic segments once an anastomosis has formed.

The self-opening devices of the invention are designed to be delivered in a side-by-side configuration. In this configuration, a self-opening device can be inserted through a trocar or other cannula to a location within a patient where the device will be deployed and coupled to a mating device. Typically, a pusher will be used to extract the self-opening device from the trocar. Once the device is pushed from the trocar, the device will spontaneously open to form a polygon. In other embodiments, non-magnetic inserts, or extruded shaped tubing, may be used to facilitate delivery of a self-opening device. Other configurations of self-opening devices, i.e., squares, hexagons, decagons, dodecagons, tetradecagons, hexadecagons, octodecagons, and icosagons, can also be delivered in a similar manner. In some instances, the pusher may have a lumen for a guide element as discussed below. In some instances, a laparoscopic manipulator (not shown) will be used to facilitate placement of the deployed device. In some embodiments, the self-opening device is held in a delivery configuration by a polymer wrap, such as shrink tubing until the device is delivered to the location of the anastomosis. In some embodiments, the shrink tubing is configured to be released with a rip cord or some other feature that allows the tubing to be simply pulled away from the magnetic device.

Because of the construction, the magnetic devices of the invention are relatively smooth and flat and present essentially uninterrupted annular faces. Because of this design, the devices do not cut or perforate tissue(s), but rather achieve anastomosis by providing steady necrotizing pressure across the contact surface between mating deployed devices. These features also reduce the risks associated with surgical access and ensure that the anastomosis is formed with the correct geometric attributes. Overall, the design ensures the patency of the anastomosis.

During deployment, the polygon-closing assembly acts as a hinge between magnetic segments while coupling the structural rigidity of individual segments 1 similar to a cantilevered beam. In other words, the tensile modulus of the polygon-closing assembly and the polygon-closing assembly's resistance to out-of-plane bending allow the forces on the distal end of the structure to be distributed across the magnetic segments. The design allows a pushing force on the proximal end of the device in a delivery configuration to reliably move the distal end of the device, e.g., out of a deployment lumen such as the working channel of an endoscope. Because the polygon-closing assembly is thin, and in close contact with the magnetic segments that are long relative to the length of their miter joints, the polygon-closing assembly can bend to accommodate miter closure with relatively small strain. However, the breadth of the polygon-closing assembly produces a high moment of inertia (stiffness) against out-of-polygonal-plane bending, thereby giving good guidance of the growing ring and providing lateral resistance to deflection during closure. Finally, the polygon-closing assembly also provides a tensile coupling between the magnetic segments, assuring that the segments do not go past the closure point and collapse inward or over top of one-another.

In many instances, it is beneficial to be able to manipulate the location of a device after it has been delivered to a tissue. While the device can be manipulated with conventional tools such as forceps, it is often simpler to manipulate the location of the deployed device with a guide element, such as a suture or wire. A variety of attachment points can be used to provide control over the location and deployment of a self-opening or a self-closing magnetic anastomosis device. The guide element may extend proximally away from the surgical field and emerge, e.g., from a port or from the proximal end of the working channel of an endoscope.

The guide element may be coupled to a single distal segment such that, upon deployment, the single distal segment results in an attachment point that provides translational freedom of movement. It is also notable that in the self-closing configuration, the guide element allows a closing force to be applied to the distal-most segment. That is, in the event that one or more segments should become entangled with tissue, or otherwise prevented from closing, a proximal pulling force with the guide element can help the device to complete self-assembly. Furthermore, once the device has achieved its deployed configuration, the device can be positioned with the guide element to be mated with another device as described above. It is envisioned that additional structures, such as a pusher, may be used to deploy the device at the desired location. The pusher will typically be formed from a rigid non-interactive material, such as Teflon™ or other polymer approved for surgical applications.

The guide element can be fabricated from a variety of materials to achieve the desired mechanical properties and bio-compatibility. The guide element may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high-density polyethylene fibers) or Kevlar™ (para-aramid fibers). In an embodiment, guide element 220 is constructed from biodegradable suture, such as VICRYL™ (polyglactin 910) suture available from Ethicon Corp., Somerville, N.J.

The guide element can be coupled to the self-closing or self-opening device with a number of different configurations and attachment mechanisms. Additionally, the guide elements can be used in the same configurations regardless of the magnetic polar configuration of the devices. The guide element may be simply tied to the device, or the guide element can be attached to the device with an adhesive, e.g., acrylate glue, or with a fastener, such as a clip, screw, or rivet.

In other embodiments, the guide element may be attached to, or configured to interact with, more than one part of the device. For example, a self-opening device, wherein a guide element may be coupled to the distal-most segment of a self-opening device, and configured to interact with radial members that facilitate assembly and placement of the device. Alternatively, two guide elements may be coupled to the hinges to facilitate conversion from a delivery configuration to a deployed configuration. Furthermore, proximal force on the guide element helps the device to close.

An alternative delivery technique includes the use of a guidewire to deliver a device to the area where an anastomosis is to be formed. The device can be self-opening or self-closing, and a procedure may involve both a self-opening and a self-closing device. Once the device has been delivered to the area, a sheath keeping the device from deploying can be removed proximally, thereby allowing the self-opening device to transform to a deployment configuration. In other embodiments, the sheath can be de-constructed, e.g., using a rip cord that is manipulated by a grasper. Once the sheath has been retracted suitably, the pusher can be used to place the device or help it to mate with a joining device. The delivery and deployment may be visualized, e.g., with fluoroscopy or ultrasound, and the device and the pusher may include markers, such as radiopaque markers, to facilitate visualization. Additionally, the device may include one or more guide elements to improve deployment or to facilitate placement.

FIGS. 1-5 show different embodiments of magnetic devices that can be used to form anastomoses. FIG. 1 shows a chain-type magnetic device, where the magnetic segments are coupled together with linkages. The chain will self-assemble into a polygon once delivered to an anatomical location. The self-assembly can be driven by selecting magnetic segments whose polarities will assume a lowest energy potential in the polygonal shape. The magnetic segments may be mitered to assure that the polygon shape is achieved. The chain-type device may include springs or tensioned members to facilitate closure into a polygon. The linkages and couplings can be formed of any resilient and biocompatible material, such as stainless steel, or polymers. The chain-type magnetic device may be delivered to an anatomical location and coupled to another chain-type magnetic device or a magnetic device of the type disclosed in the other applications listed at the beginning of this disclosure and incorporated by reference herein. FIG. 2 shows a self-opening chain-type device similar to FIG. 1. The materials of construction and the method of self-opening (e.g., miters, springs, tensioned members) are the same as discussed above with respect to FIG. 2.

Figure 3:
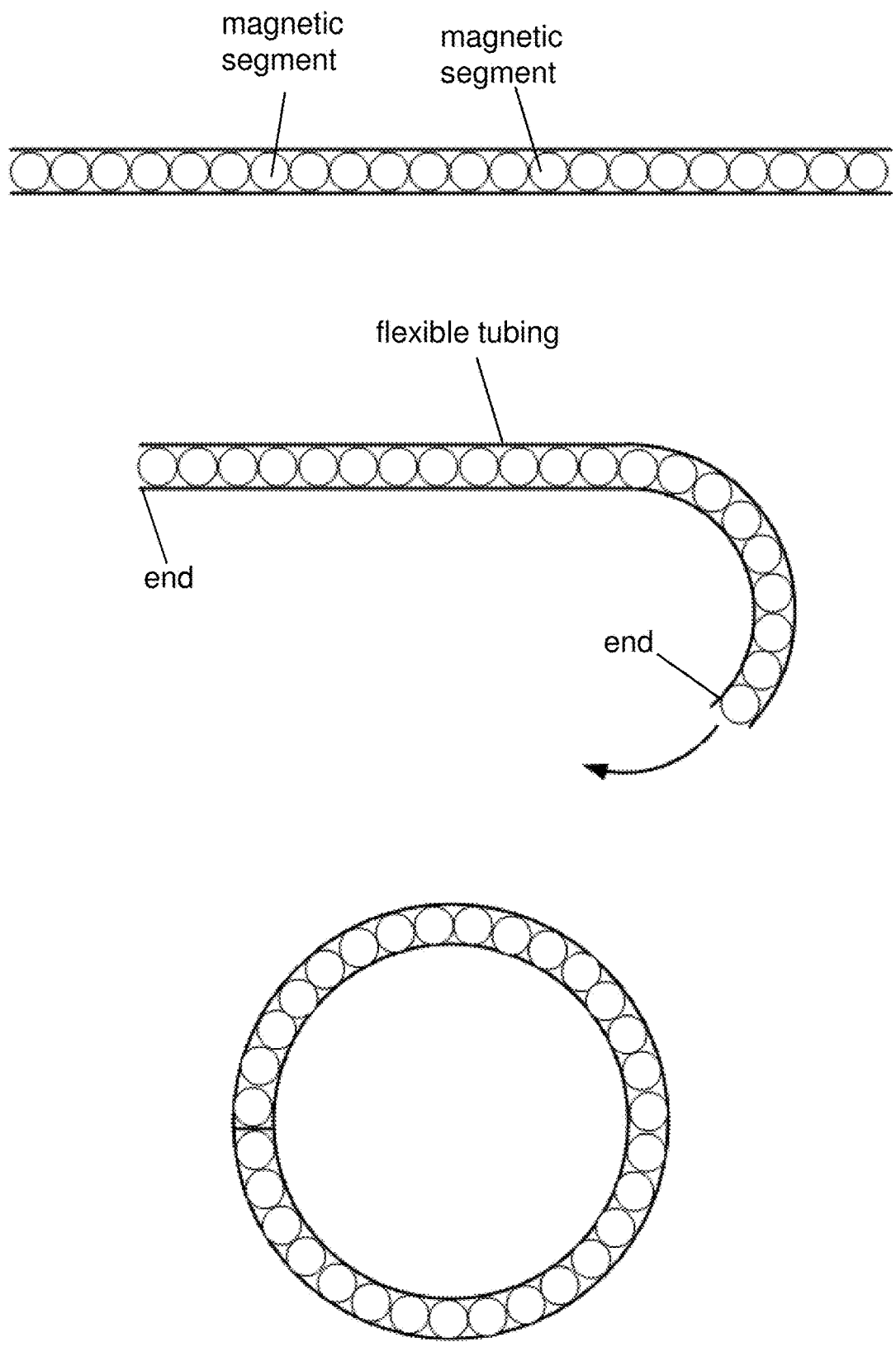
FIG. 3 depicts an embodiment of a self-closing magnetic device for use to form an anastomosis.
Figure 4:
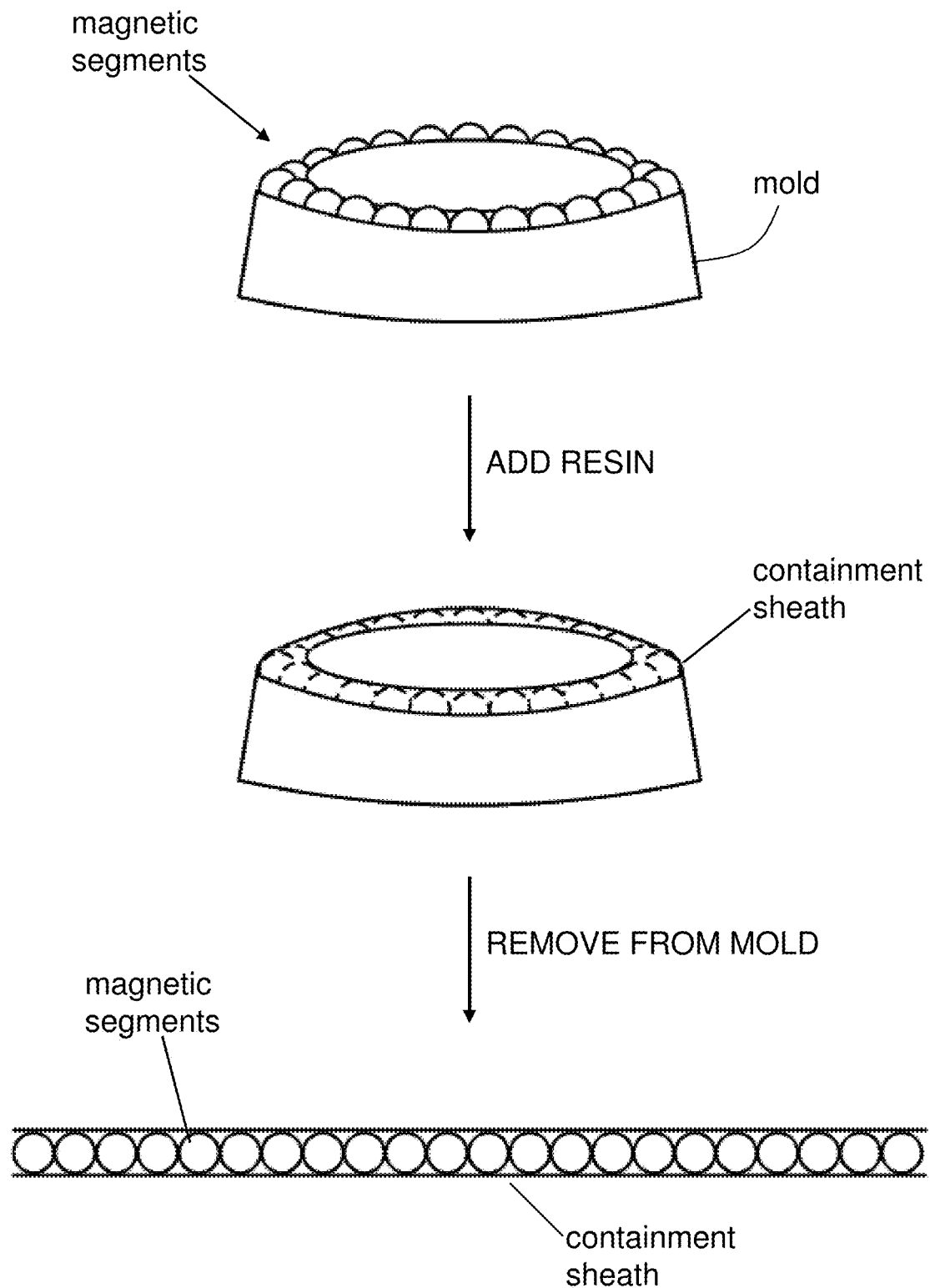
FIG. 4 depicts a method of constructing the self-closing magnetic device of FIG. 3.

FIG. 3 shows an alternative embodiment using spherical magnetic balls that are held together with flexible tubing or some other retaining device. As shown in FIG. 4, the device can be constructed by arranging a group of balls in a mold and then delivering a resilient polymer to the mold. Once finished the polymer will keep the balls together, yet it will be sufficiently flexible to be straightened for delivery via a lumen of a medical device, for example, the working channel of an endoscope or a catheter, or a trocar. The completed device may need to be cut to provide a separation point. Similar methods can be used to form a self-opening magnetic device of a similar configuration. The methods of construction are not limited to a mold or die, however, as the magnetic spheres can be arranged in a circle and then dip coated to keep them together. While not shown in FIGS. 3 and 4, wires, or other stiffening members may be added to minimize out-of-plane bending in the finished device.

Figure 5:
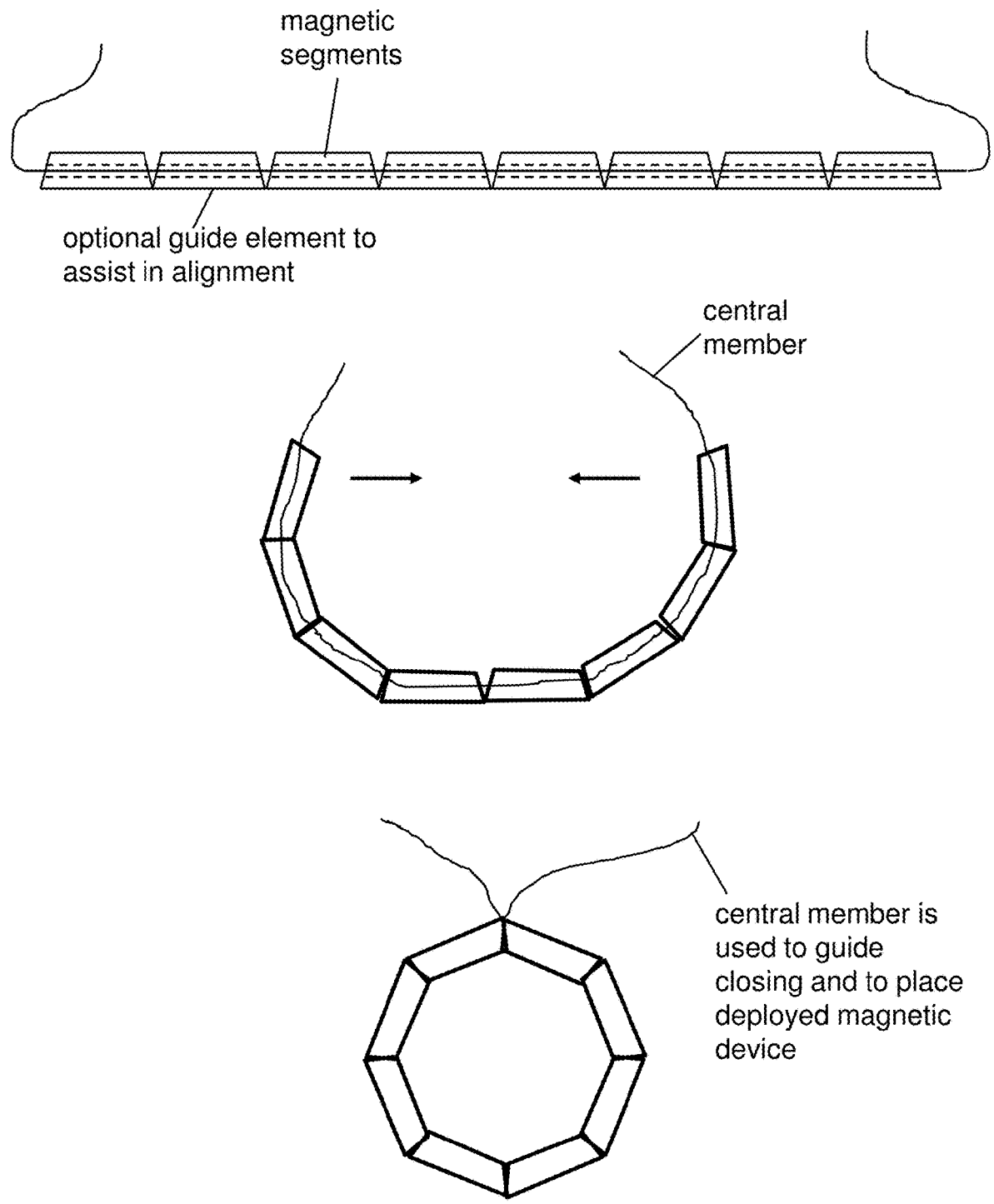
FIG. 5 depicts a self-closing magnetic device for forming an anastomosis. The device includes a central member to couple the magnetic segments. The central member may also facilitate placement of the device.
Figure 6:
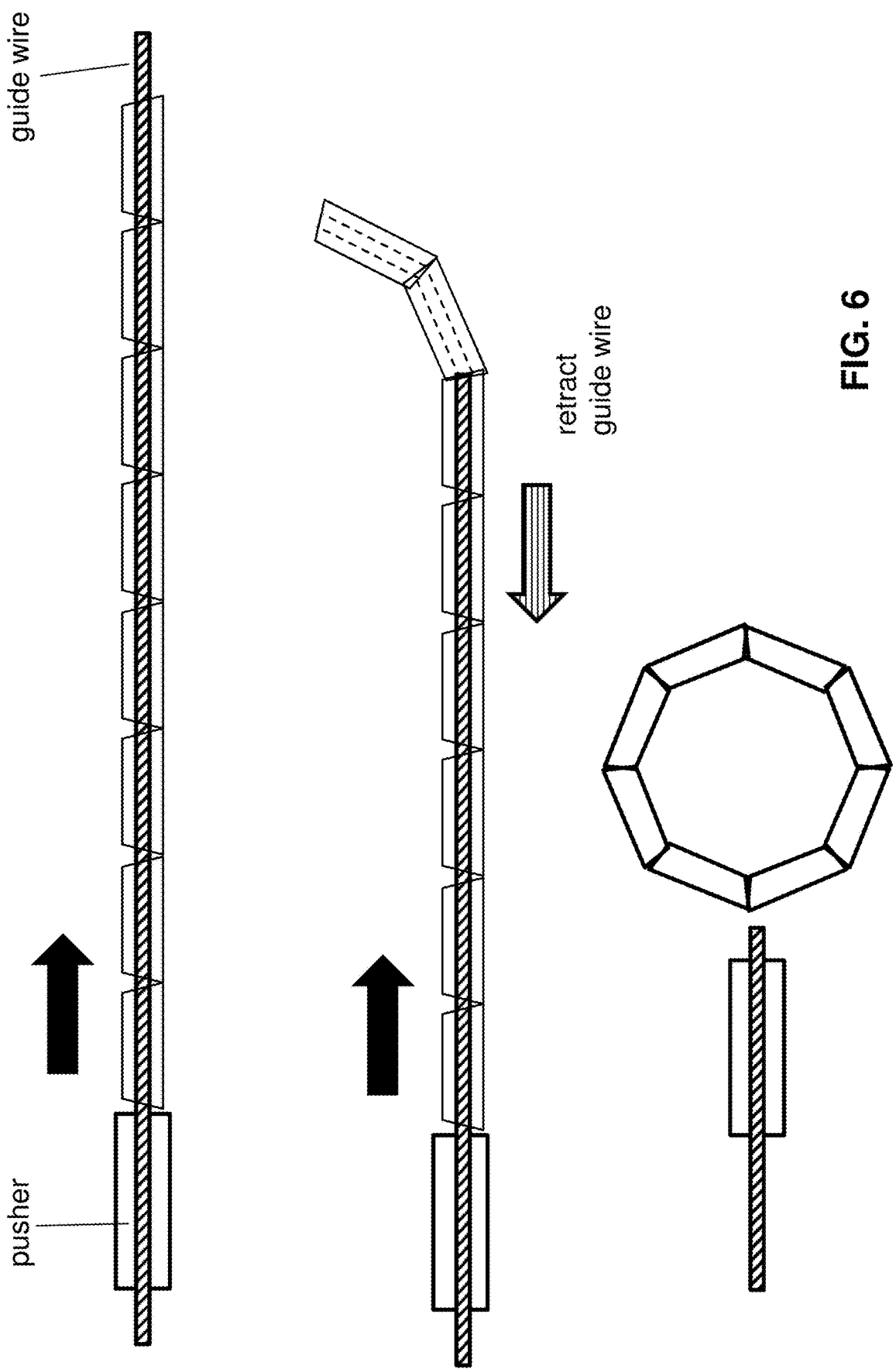
FIG. 6 depicts a method of deploying of a self-closing magnetic device that is delivered over a guide wire.
Figure 7:
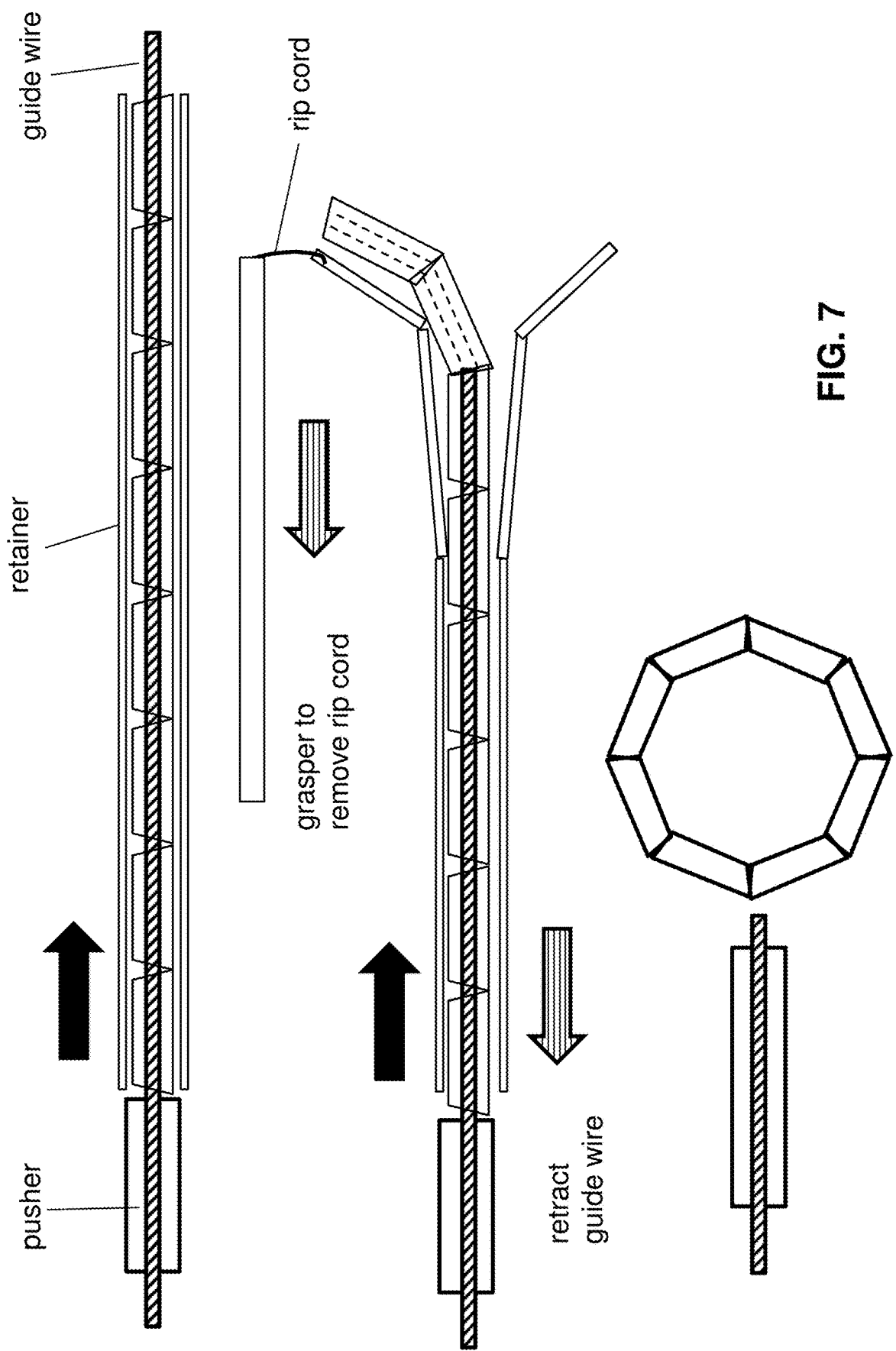
FIG. 7 depicts a method of deploying of a self-closing magnetic device that is delivered over a guide wire. The device is retained in a delivery configuration by a biocompatible polymer that can be removed by manipulating a rip cord.
Figure 8:
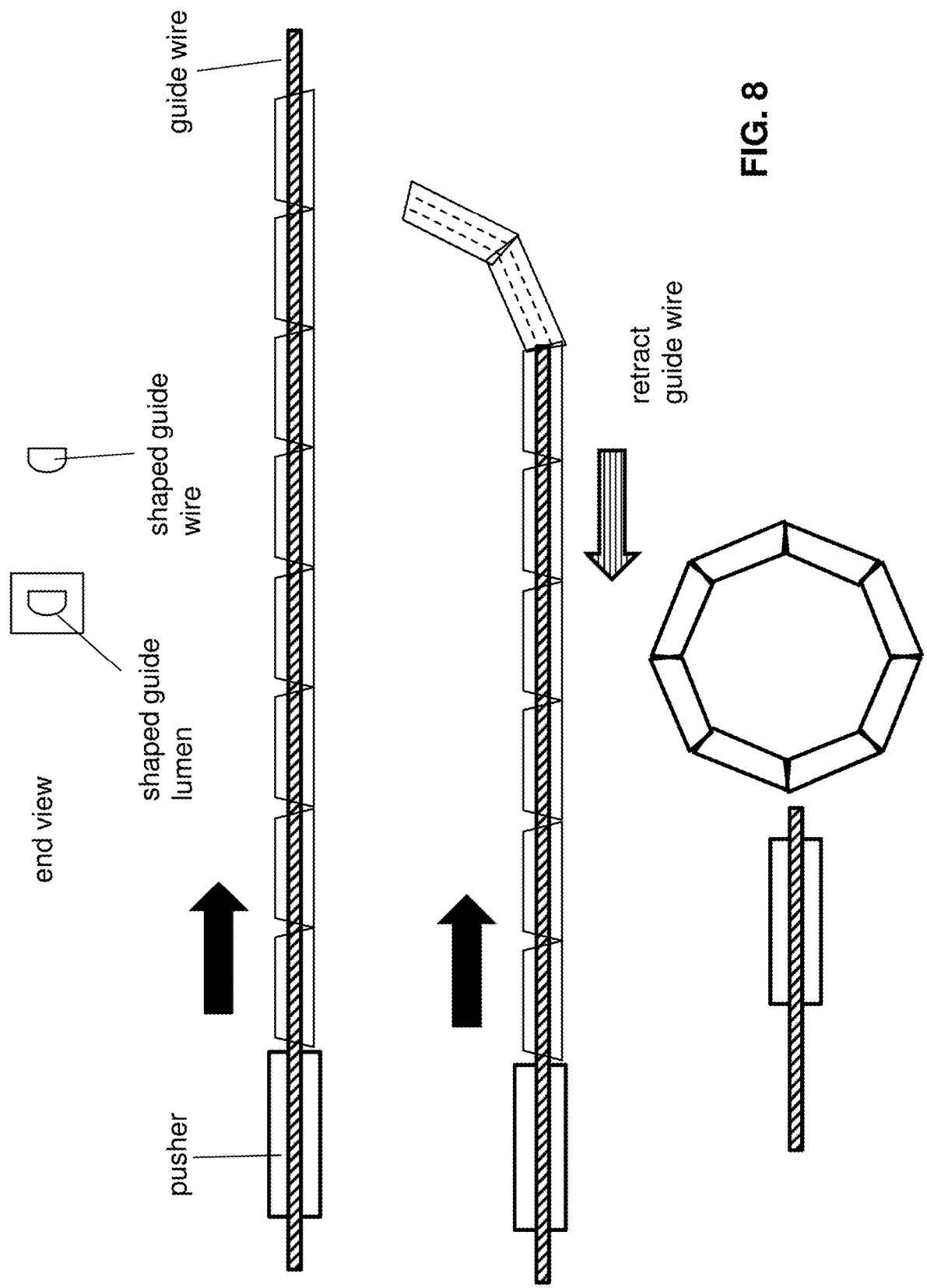
FIG. 8 depicts a self-closing magnetic device having a shaped guide lumen that maintains an orientation of the magnetic segments as they pass along a mating guide wire having the same shape.

FIGS. 5-8 show different embodiments of a self-closing device for forming an anastomosis consistent with the present disclosure. FIG. 5 shows a device including a central member to couple the magnetic segments together. The central member may also facilitate placement of the device. FIG. 6 depicts a method of deploying of a self-closing magnetic device that is delivered over a guide wire. FIG. 7 depicts a method of deploying of a self-closing magnetic device that is delivered over a guide wire, wherein the device is retained in a delivery configuration by a biocompatible polymer that can be removed by manipulating a rip cord. FIG. 8 depicts a self-closing magnetic device having a shaped guide lumen that maintains an orientation of the magnetic segments as they pass along a mating guide wire having the same shape.

As shown, the self-closing compression anastomosis device includes an assembly of magnetic segments coupled end-to-end and configured to transition between a delivery configuration, in which the magnetic segments are aligned end-to-end in a single-file arrangement defining a linear assembly having first and second ends, and a deployed configuration, in which the linear assembly forms a polygon by joining of the first and second ends. Each of the magnetic segments is configured to be coupled to a guide member. When in the delivery configuration, the assembly of magnetic segments is sized to fit within a working channel of an access device and to be delivered to an anatomical structure within a patient. The access device may include, but is not limited to, an endoscope, a laparoscope, a trocar, and a cannula.

As shown in FIG. 5, the self-closing device that includes a series of lumens through the magnetic segments to allow a central member to be run through the magnetic segments to facilitate assembly. The central member can be fabricated from a variety of materials to achieve the desired mechanical properties and bio-compatibility. For example, the central member may be constructed from metal, e.g., wire, e.g., stainless steel wire, or nickel alloy wire. In some embodiments, the central member may be thermally-programmed so as to assume the desired shape, e.g., a circle, when exposed to body temperature, for example. Accordingly, the central member may be a wire, such as a stainless steel or nitinol wire. In other embodiments, the central member may be constructed from suture, wherein the central member may be constructed from natural fibers, such as cotton or an animal product or from polymers, such as biodegradable polymers, such as polymers including repeating lactic acid, lactone, or glycolic acid units, such as polylactic acid (PLA). The central member may also be constructed from high-tensile strength polymers, such as Tyvek™ (high-density polyethylene fibers) or Kevlar™ (para-aramid fibers). In an embodiment, central member is constructed from biodegradable suture, such as VICRYL™ (polyglactin 910) suture available from Ethicon Corp., Somerville, N.J.

In some embodiments the central member can be used to direct placement after the device has self-assembled. In some embodiments, additional mechanical features can be bound between the magnetic segments to minimize out-of-plane motion during delivery and deployment, in similar manner as described with respect to the exoskeleton.

In some embodiments, such as shown in FIGS. 6 and 7, the guide member includes a guidewire and the assembly is configured such that removal of the guidewire from the lumens of magnetic segments facilitates transitioning of the assembly from the delivery configuration to the deployed configuration. For example, as shown in FIG. 6, the guidewire is configured to prevent self-assembly of the magnetic segments into the polygon while positioned within the lumen of the at least one magnetic segments and the assembly spontaneously converts from the delivery configuration to the deployed configuration once the guidewire is removed from the lumen of the at least one magnetic segment. Accordingly, the assembly of magnetic segments shown in FIGS. 6-8 is configured to translate along a length of the guide member when transitioning from the delivery configuration to the deployed configuration.

Once the device has been delivered to the desired location, the guidewire can be simply retracted to leave a deployed device. In other embodiment, a retainer may be used to facilitate placement and self-assembly. The retainer may be a separate catheter, or the retainer may be removable, e.g., with a rip cord, as shown in FIG. 7. In other embodiments, the retainer could be designed to weaken when exposed to moisture plus body temperature to such a point at which the magnet assembly pops open. Using such a system, a physician could watch, using fluoroscopic imaging, the device until the device "popped open." A complimentary device may require active components, such as a guide wire, or radial elements, described elsewhere, to direct the complimentary device to a magnet that simply "pops open."

In some embodiments, the magnetic devices have guide elements that are shaped to mate with specially-formed guide wires. For example, as shown in FIG. 8, the guide element may include a lumen of one or more magnetic segments having a defined cross-sectional shape corresponding to a shape of the guide member so as to limit rotational movement of the associated magnetic segment during translation of the magnetic segment along a length of the guide member. The lumen may include a non-circular cross-sectional shape, for example. The guide member may include a cross-sectional shape corresponding to the cross-sectional shape of the lumen of the at least one magnetic segment. Because the guide elements can only traverse the guide wire in one orientation, the orientation of the device is maintained as it traverses the guide wire. Conversely, it is possible to rotate the magnetic device close to or at the delivery site by rotating the guide wire.

Figure 9:
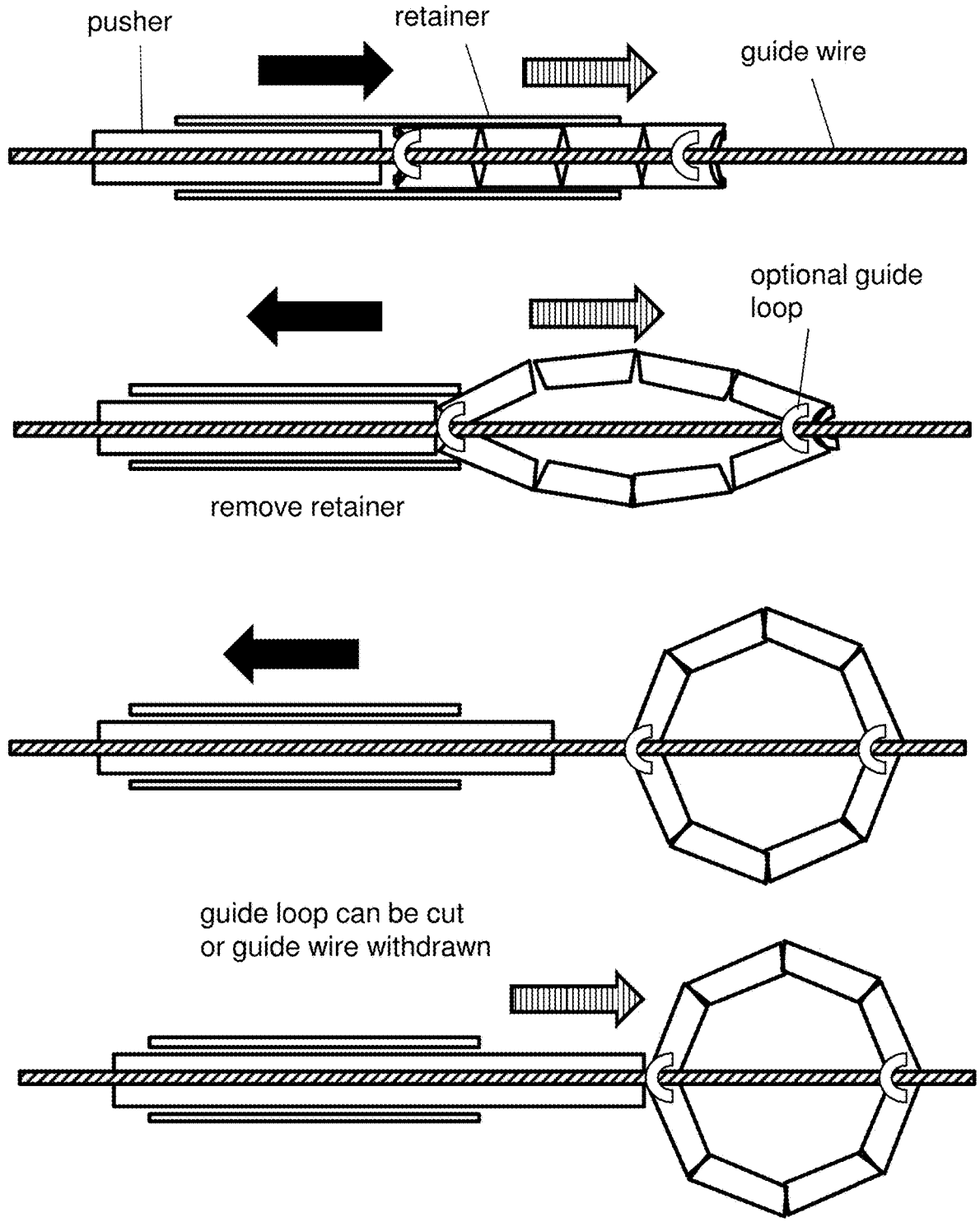
FIG. 9 depicts a method of deploying a self-opening magnetic device that is delivered over a guide wire.
Figure 10:
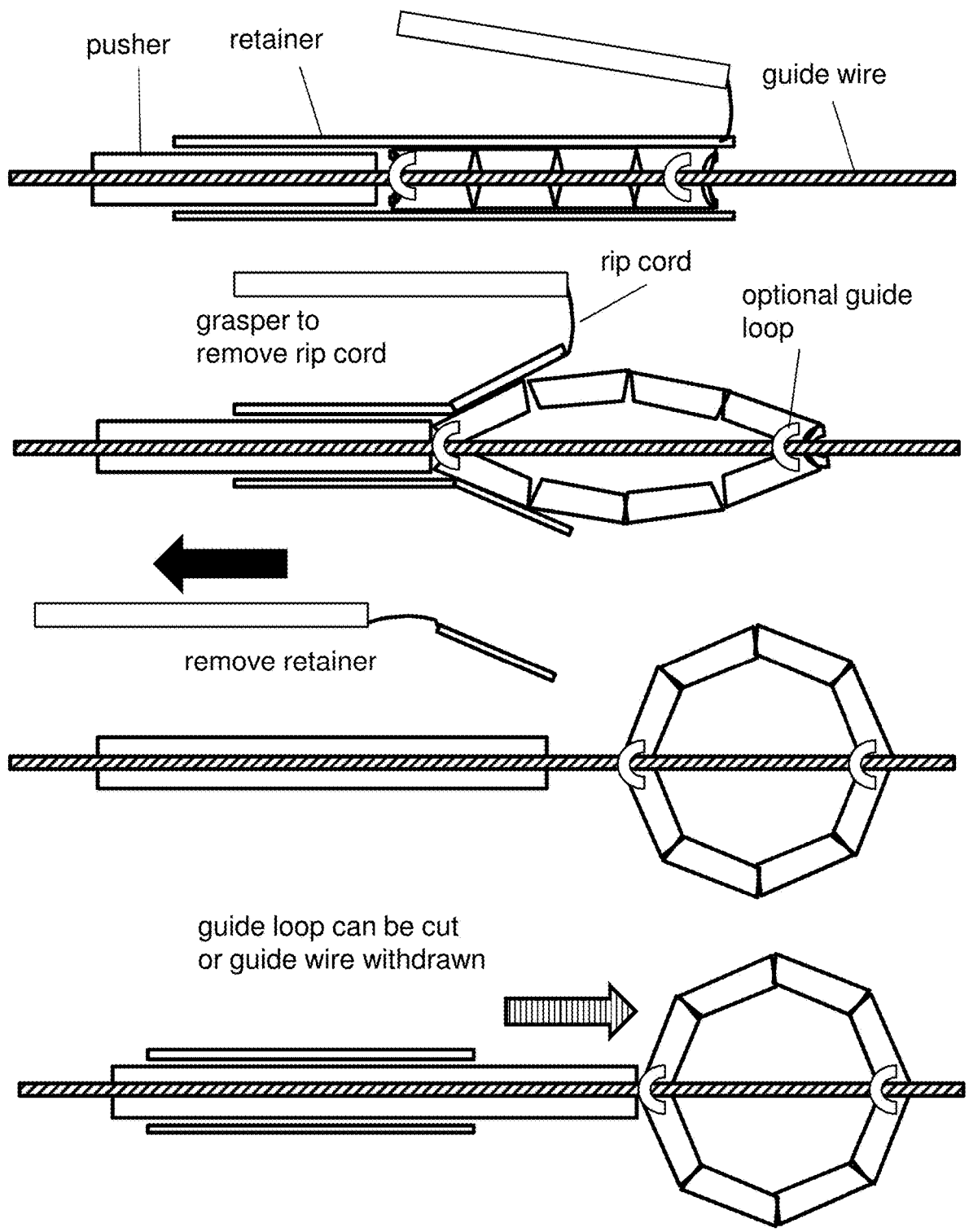
FIG. 10 depicts a method of deploying of a self-opening magnetic device that is delivered over a guide wire. The device is retained in a delivery configuration by a biocompatible polymer that can be removed by manipulating a rip cord.
Figure 11:
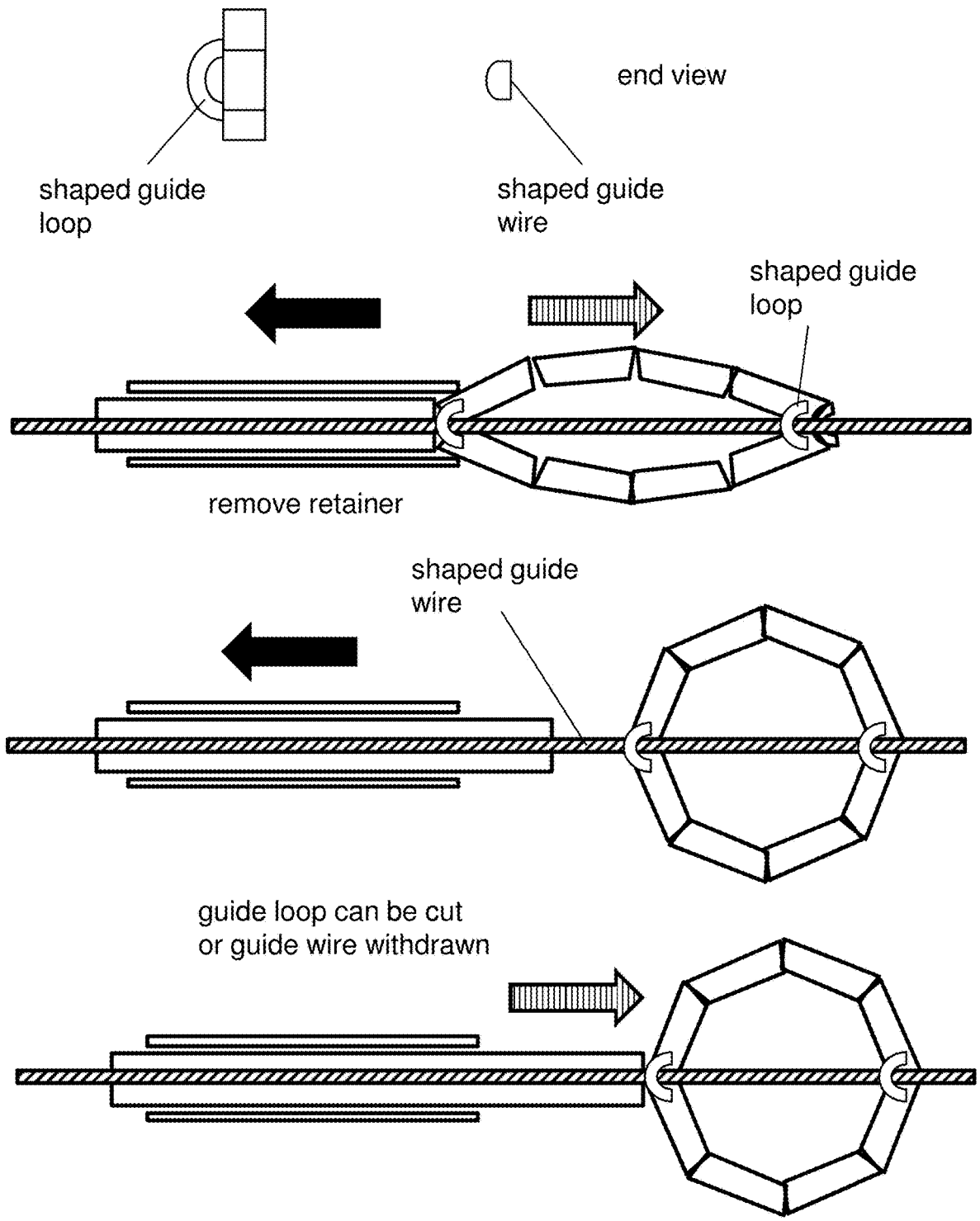
FIG. 11 depicts a self-opening magnetic device having a shaped guide loop that maintains an orientation of the magnetic device as it is passed along a mating guide wire having the same shape.

FIGS. 9-11 show different embodiments of a self-opening device for forming an anastomosis consistent with the present disclosure. FIG. 9 depicts a method of deploying a self-opening magnetic device that is delivered over a guide wire. FIG. 10 depicts a method of deploying a self-opening magnetic device that is delivered over a guide wire and is retained in a delivery configuration by a biocompatible polymer that can be removed by manipulating a rip cord. FIG. 11 depicts a self-opening magnetic device having a shaped guide loop that maintains an orientation of the magnetic device as it is passed along a mating guide wire having the same shape.

As shown, the self-opening compression anastomosis device may an assembly of at least four magnetic segments coupled end-to-end to form a polygon having an out-of-plane axis, wherein each magnetic segment has a north magnetic pole and a south magnetic pole. The assembly may include a first pair of magnetic segments coupled together with a first connection member and a second pair of magnetic segments coupled together with a second connection member. The assembly includes a delivery configuration in which the magnetic segments are aligned in two rows, the two rows being joined by the first and second connection members or one or more additional connection members coupling the first and second pairs of magnetic segments to one another, and a deployed configuration in which the magnetic segments form an open polygon based, at least in part, on a force provided by at least one of the first and second connection members or the additional connection members.

At least one of the magnetic segments includes a guide element configured to receive a guide member therethrough, such that the assembly of magnetic segments is configured to translate along a length of the guide member when transitioning from the delivery configuration to the deployed configuration.

In some embodiments, the guide element is a loop or sleeve having a lumen for receiving the guide member therethrough so as to allow the assembly to translate along the guide member. In some embodiments, the lumen of the loop or sleeve has a defined cross-sectional shape corresponding to a shape of the guide member so as to limit rotational movement of the associated magnetic segment during translation of the magnetic segment along a length of the guide member. For example, the lumen may include has a non-circular cross-sectional shape. Accordingly, the guide member may include a cross-sectional shape corresponding to the cross-sectional shape of the lumen of the loop or sleeve.

In some embodiments, when in the delivery configuration, the assembly of magnetic segments is sized to fit within a channel of a retaining member or sleeve configured to maintain the assembly in the delivery configuration until desired delivery of the assembly to an anatomical structure within a patient. Upon separation of the assembly from the channel of the retaining member or sleeve, the assembly is configured to spontaneously convert from the delivery configuration to the deployed configuration. When transitioning from the delivery configuration to the deployed configuration, the assembly is configured to translate along a length of the guide member. The guide member is configured to facilitate manipulation and placement of the compression anastomosis device when in the deployed configuration. The retaining member or sleeve is configured to fit within a working channel of an access device and to be delivered to an anatomical structure within a patient. The access device may include, but is not limited to endoscope, a laparoscope, a trocar, and a cannula.

As shown in FIG. 9, the device may use a retainer to keep the device in delivery configuration. The device is moved along the guide wire until the desired location, at which point the retainer is removed. The retainer may be a separate catheter or over-sheath, or the retainer may be a removable material such as heat-shrink tubing or a similar polymer. In some embodiments, as show in FIG. 10, the retainer may include a rip cord, or some other mechanism to cause the retainer to pull away from the device, thus allowing the device to attain a deployment configuration. In some embodiments the device may include a guide loop to make sure that the device rides down the guide wire to the desired location. The guide loop may be constructed from, e.g., suture, and may be cut to deploy the device. In another embodiment, the guidewire may be simply retracted to leave the device at the desired location.

In some embodiments, the magnetic devices have guide elements that are shaped to mate with specially-formed guide wires. For example, as shown in FIG. 11, the guide element may include a lumen having a defined cross-sectional shape corresponding to a shape of the guide member so as to limit rotational movement of the associated magnetic segment during translation of the magnetic segment along a length of the guide member. The lumen may include a non-circular cross-sectional shape, for example.

The guide member may include a cross-sectional shape corresponding to the cross-sectional shape of the lumen of the at least one magnetic segment. Because the guide elements can only traverse the guide wire in one orientation, the orientation of the device is maintained as it traverses the guide wire. Conversely, it is possible to rotate the magnetic device close to or at the delivery site by rotating the guide wire.

Figure 12:
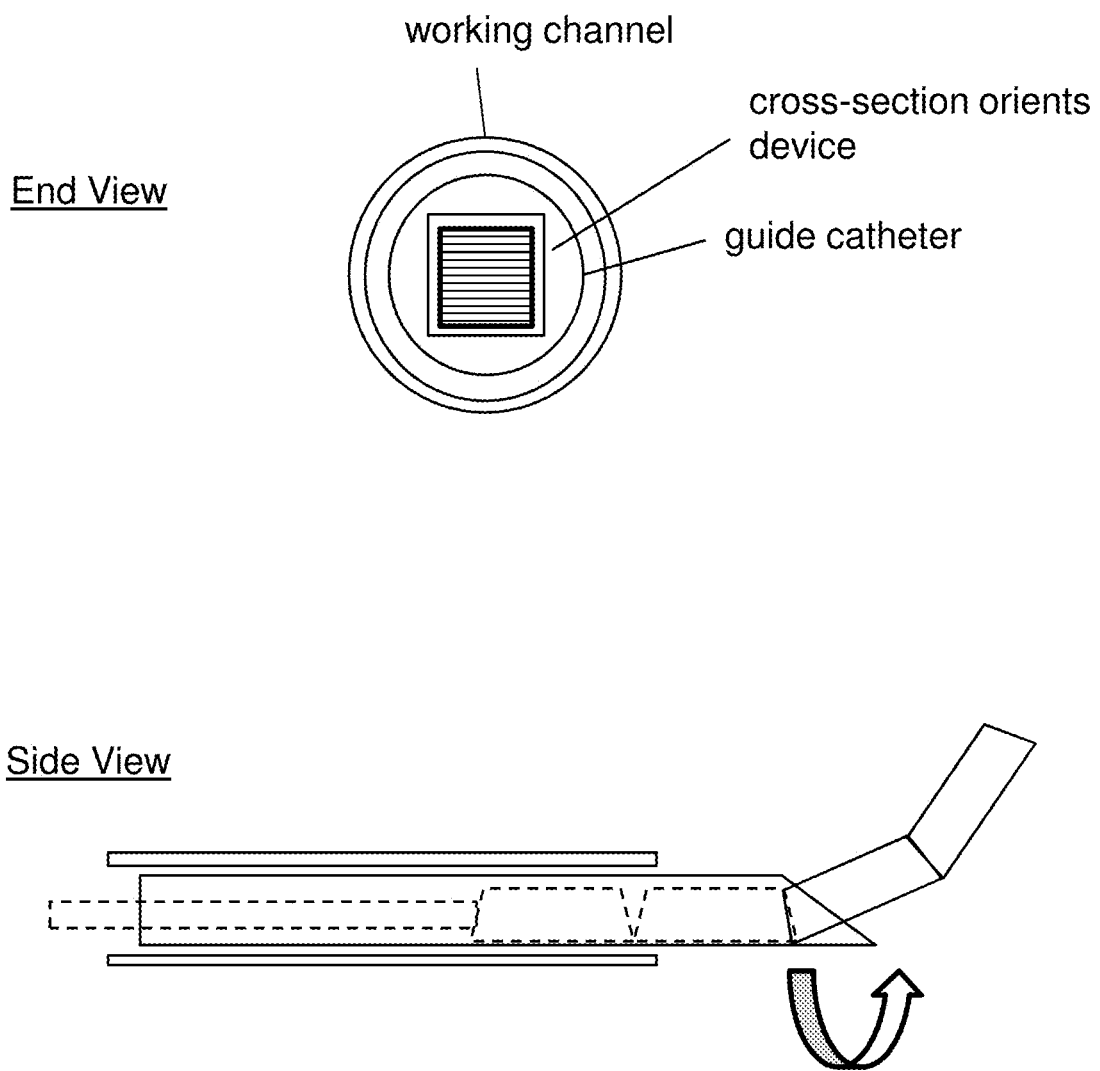
FIG. 12 depicts two embodiments of delivery catheters designed to facilitate rotation of the magnetic device at the site of the anastomosis.

FIG. 12 shows a specialty catheter for delivering a device of the invention and to provide rotational control at the point of deployment. As shown in FIG. 10, a delivery catheter may have a shaped opening to confine the device in a direction. The opening may be square, or other shape, depending upon the cross section of the device. During deployment, the catheter could be rotated at the proximal end, e.g., external to the endoscope, so that the magnetic device can be delivered with a specific rotational configuration. This may facilitate placement of a mating device, once a first device has been placed.

Figure 13:
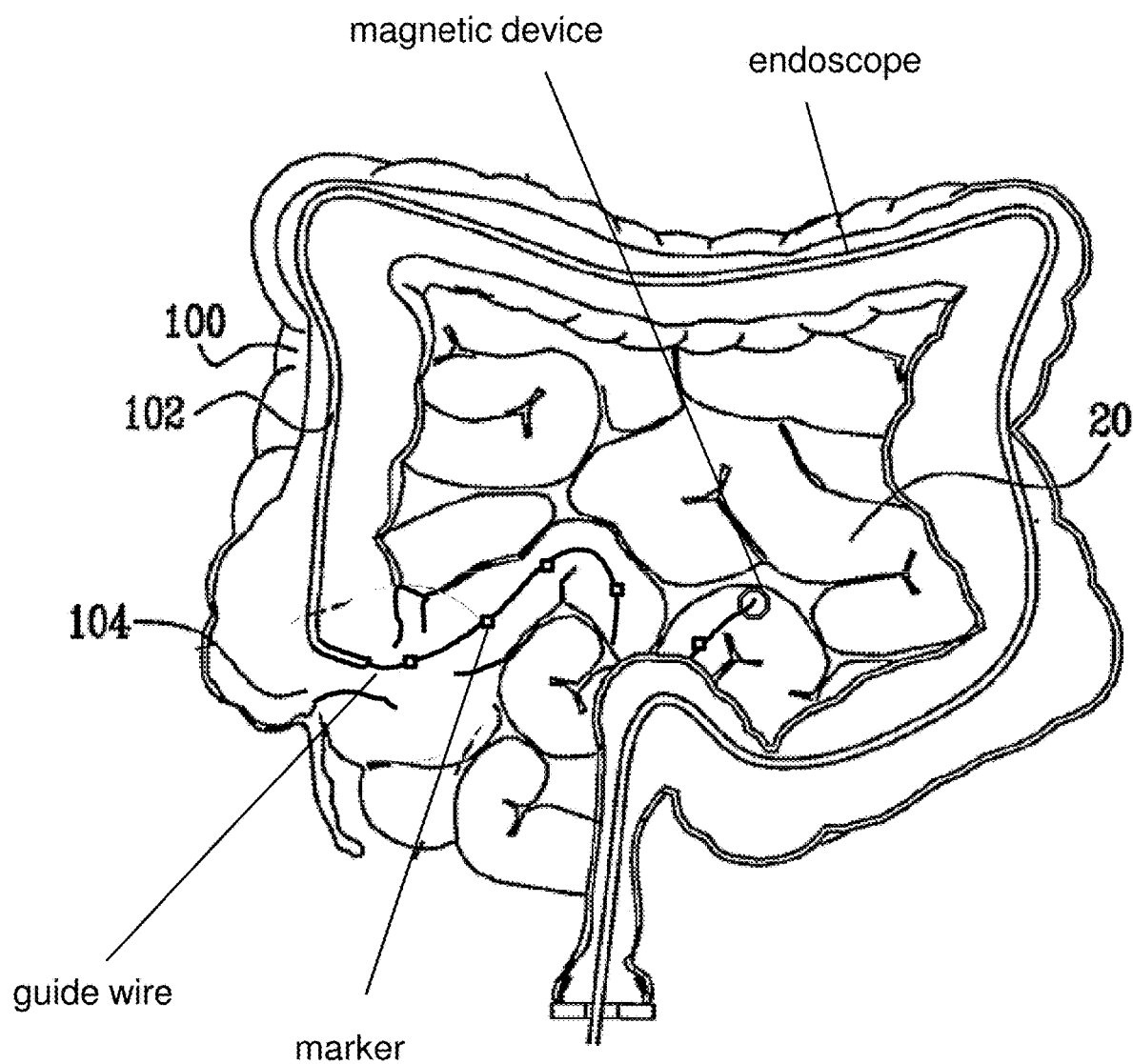
FIG. 13 shows delivery of a magnetic device to the small intestine via an endoscope delivered through the rectum. In some embodiments, a guide wire may be delivered through the endoscope to extend the reach of the endoscope. The guidewire may include one or more markers to facilitate distance measurements in a fluoroscopic image.

FIG. 13 shows an alternative embodiment for delivery of a magnetic device. As shown in FIG. 11, a guide wire (or a guide catheter) may be extended beyond the end of an endoscope to allow a magnetic device to be placed deep within the small intestine as accessed via the colon. To facilitate visualization under fluoroscopy, the guide wire (or guide catheter) may include radiopaque markers at preset distances. Other features, such as a deflectable, and/or steerable, and/or bendable distal tip may be incorporated to help a user more easily traverse tortuous anatomy to arrive at the desired deployment location.

Figure 14:
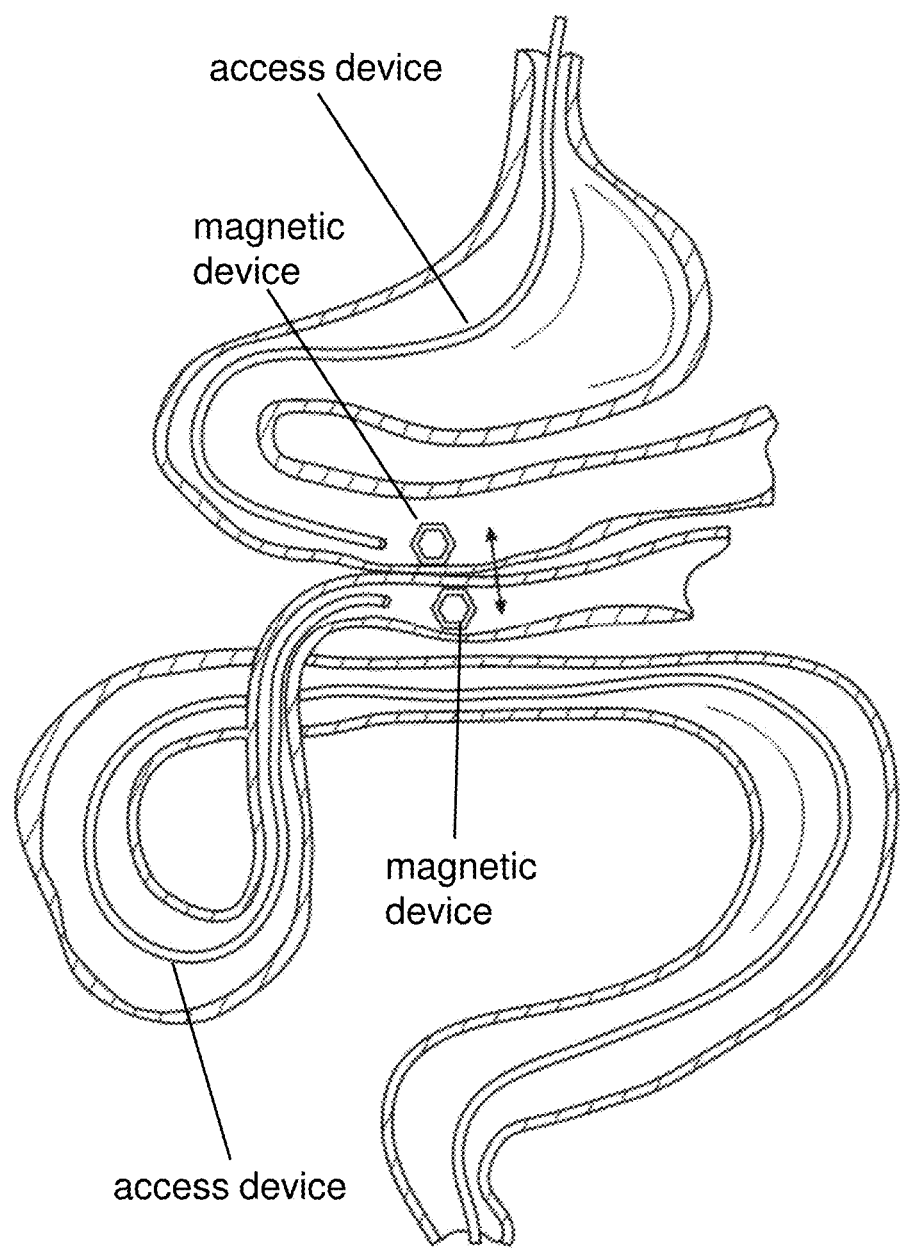
FIG. 14 shows joining two magnetic devices delivered via an upper endoscopy and a colonoscopy. In preferred embodiments, the magnetic devices are joined at a section of small intestine about 40-80 cm beyond the ileocecal valve.

FIG. 14 shows the delivery of devices via an upper endoscope and a lower endoscope (colonoscopy). For the purposes of controlling metabolic disease, such as diabetes, it may be beneficial to create an anastomosis approximate 40-80 cm up the small intestine past the ileocecal valve. For example, it may be beneficial to create an anastomosis approximately 45 cm from the ileocecal valve, or 50 cm from the ileocecal valve, or 55 cm from the ileocecal valve, or 60 cm from the ileocecal valve, or 65 cm from the ileocecal valve, or 70 cm from the ileocecal valve, or 75 cm from the ileocecal valve. In some embodiments, it may be beneficial to create more than one anastomosis in this region, such as two or three or four anastomoses.

FIGS. 15 and 16 show embodiments of devices for sensing the position, rotation, overlap, and/or camber between the two devices. Such systems will allow a user to know when maximum overlap has been achieved. In one embodiment, e.g., shown in FIG. 15, the devices may include a sensor, such as an RFID, or some other proximity sensor that can be used to verify that the devices are overlapping and substantially parallel. In other embodiments, the sensors shown in FIG. 15 may be replaced with radiopaque markers that help a user to visualize the overlap via fluoroscopy or other imaging. As shown in FIG. 16, it is also possible to observe/confirm the quality of overlap by measuring an inductive current created in the second device by a current provided to the first device. Other techniques may include a combination of sensors and/or inductive coupling and/or imaging.

Figure 17:
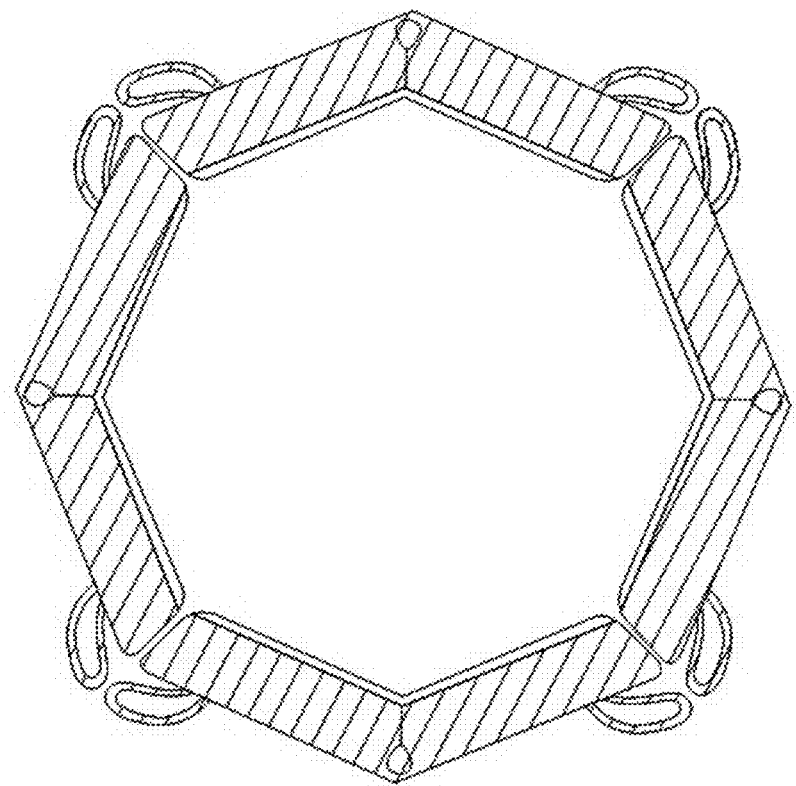
FIG. 17 depicts a magnetic device that can be pulled apart to facilitate removal after it has been coupled to a mating device.
Figure 18:
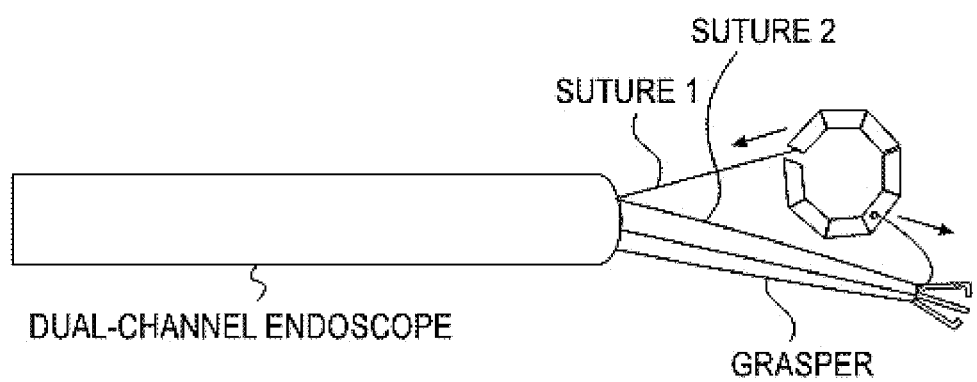
FIG. 18 depicts opening and removal of a self-closing magnetic device.
Figure 19:
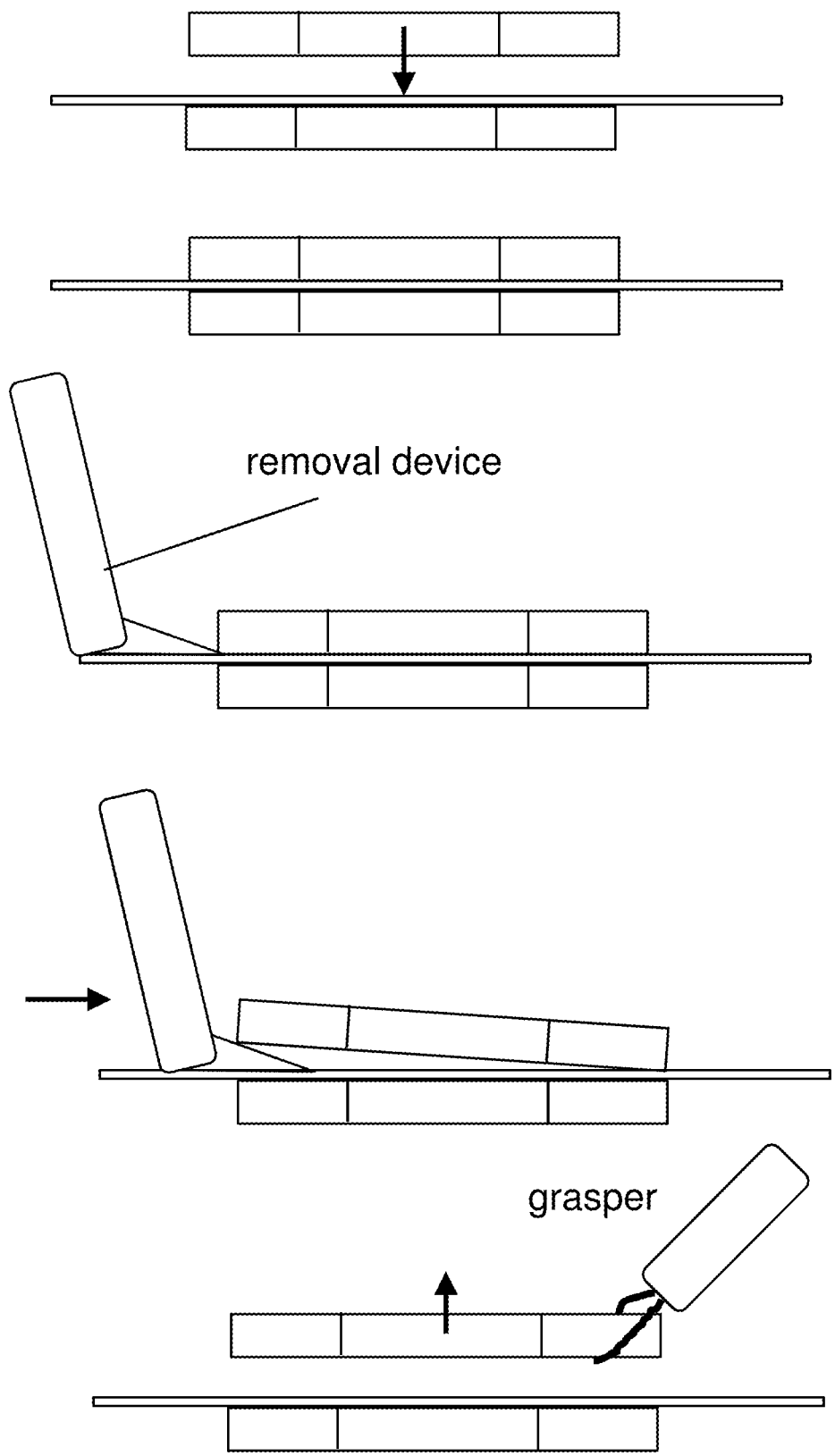
FIG. 19 depicts coupling of two magnetic devices and decoupling with a decoupling tool and a grasper.
Figure 20:
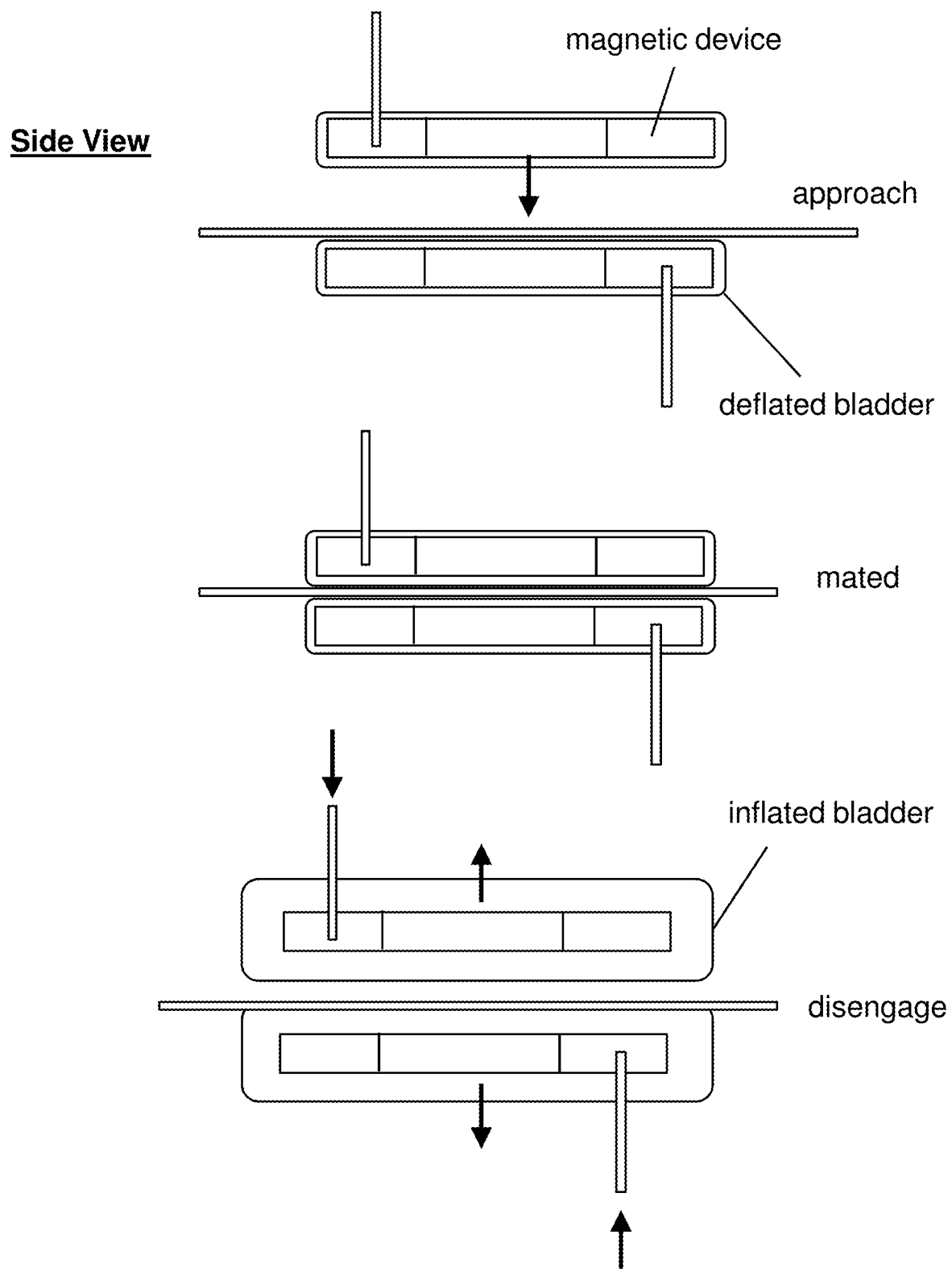
FIG. 20 depicts a magnetic device including an inflatable covering that can be used to push deployed magnetic devices apart.

FIGS. 17-20 show a variety of configurations and methods than can be used to cause coupled devices to disengage once they have been placed. As shown in FIG. 17, a device may be designed with a number of loops that allow a first device to be pulled away from a second device, e.g., using a grasper, as shown in FIG. 18. In other embodiments, the device may be designed to be pulled apart by grasping the loops and pulling a segment away from the remaining magnetic segments. FIG. 19 shows an alternative technique in which a specialty removal tool is pushed between the coupled magnetic devices to decouple the devices. Once the devices have been separated sufficiently the devices can be removed using a grasper or another suitable tool. In another alternative embodiment, e.g., shown in FIG. 20, each device is surrounded with a bladder that is in fluid communication with a reservoir external to the body. In the event that the devices need to be removed, the bladders are filled with a fluid, such as saline, causing the bladders to inflate and push the devices from each other, causing them to decouple. When the devices of FIG. 20 are deployed successfully, the bladders will not interfere with the quality of the anastomosis. Additionally, the lumens coupled to the inflation fluid can be severed with the use of a cutting instrument and then the fluid lumens removed from the subject.

Figure 22:
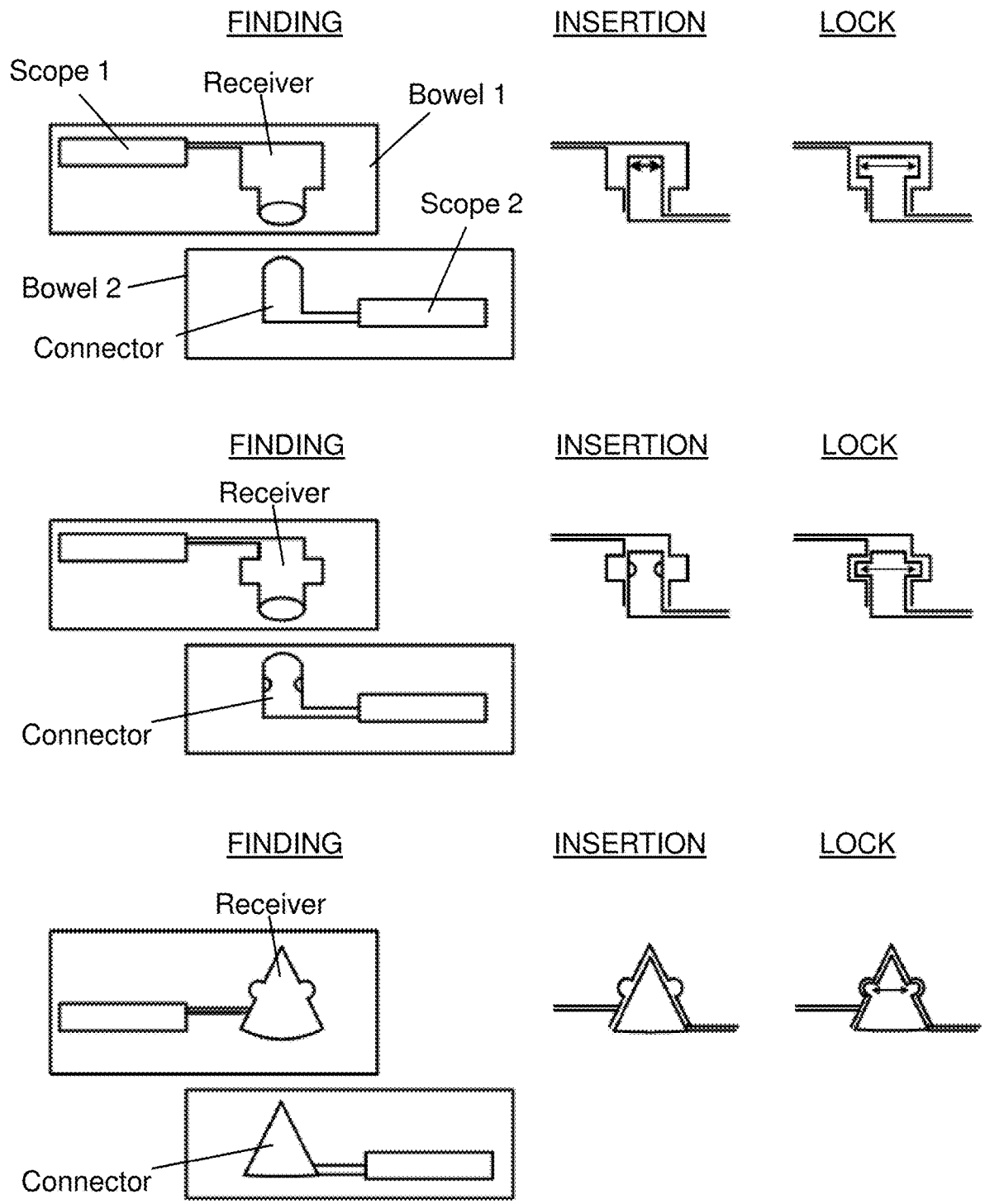
FIG. 22 depicts alternative constructions of the coupling devices shown in FIG. 26.

FIGS. 21 and 22 depict a non-magnetic coupling to be used to join bowel. The receiver and the connector are delivered via endoscope to different sections of bowel, however the device could be used to join other tissues that are not bowel. The receiver is designed to receive the connector and form a coupling that maintains the two segments of bowel together. Once the connector is in place, an actuator, or some other locking mechanism, such as a spring lock, flange, anchor, etc., keeps the receiver and coupler together, creating a passage between the segments of bowel. In some embodiments, a stoma is not created in either segment of bowel, and the compressive force of the two segments causes the tissue to necrose and an anastomosis to form. In other embodiments, one or more holes may be created to facilitate coupling of the receiver and connector. In some embodiments, the connector may include a cutting distal surface to facilitate passage through the tissue. Once the anastomosis has been formed, the coupled device will fall away from the tissues and pass from the subject.

Figure 23:
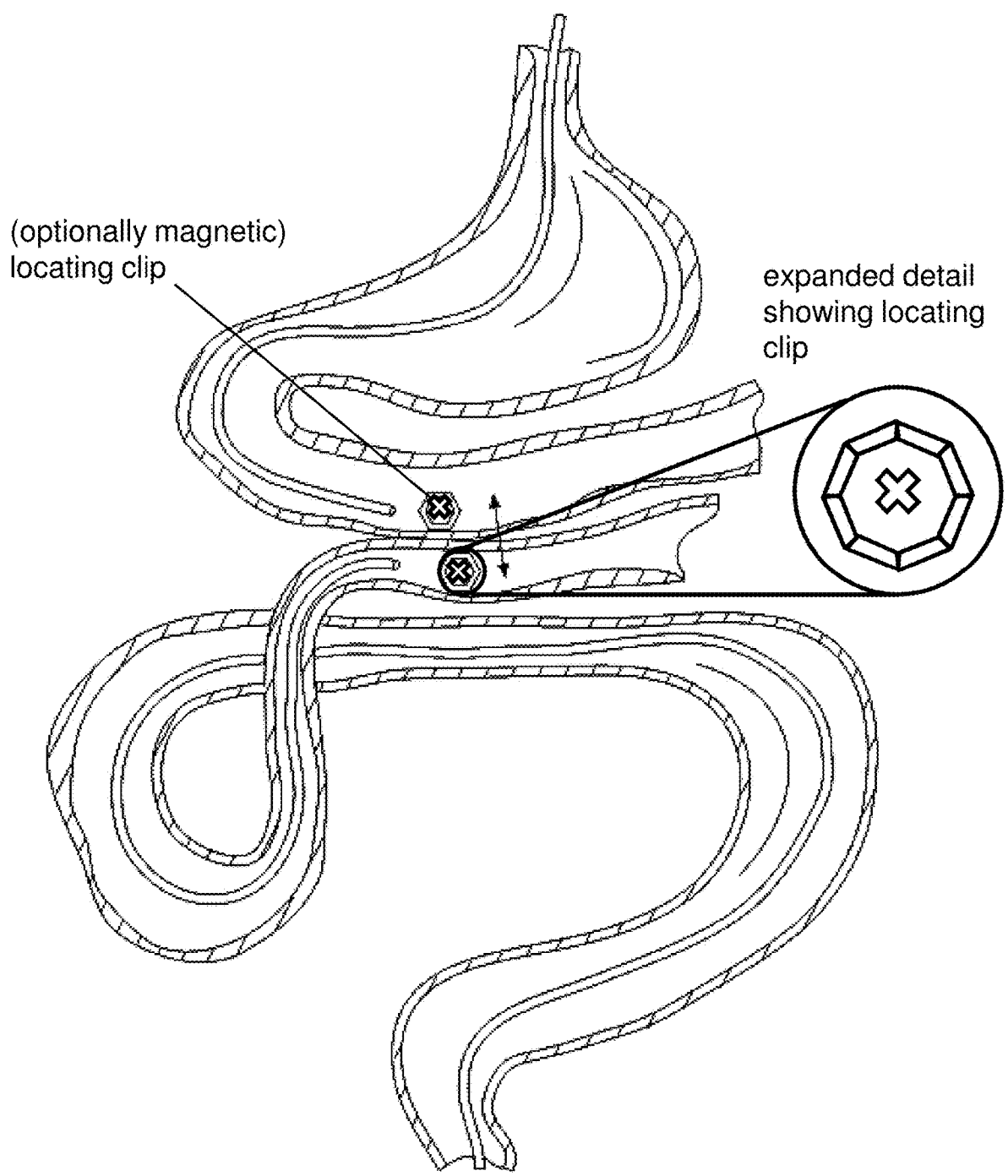
FIG. 23 depicts deployable clips that assist with location of an anatomical target and/or placement of a magnetic device. The clips are optionally magnetic or non-magnetic.
Figure 24:
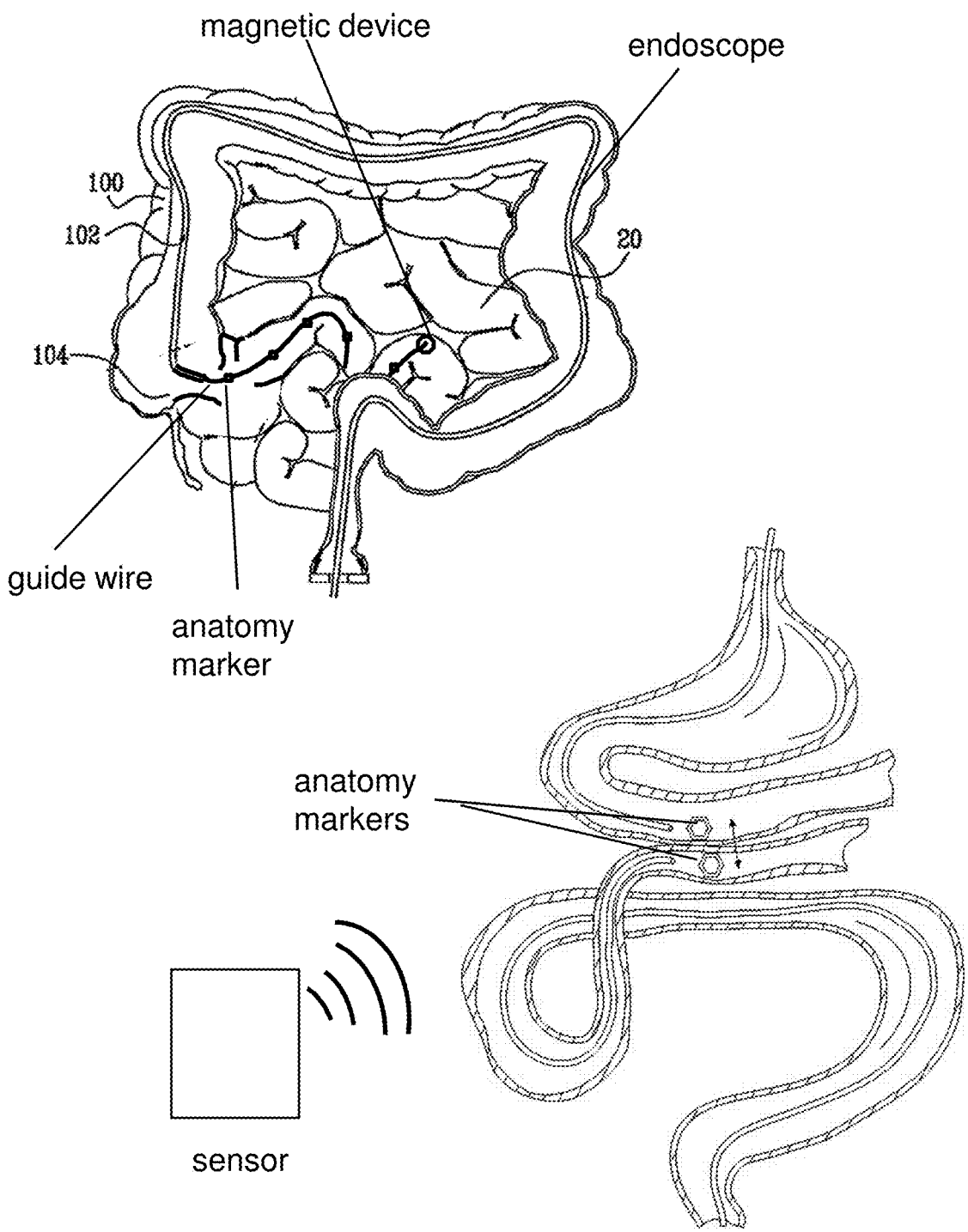
FIG. 24 depicts location of certain anatomical targets, such as the ileocecal valve or locations in the small intestine where an anastomosis should be formed. The targets may be located with fluoroscopy, ultrasound, or visualization through a scope.

FIGS. 23 and 24 depicts methods and devices for locating anatomical structures via imaging and/or with visualization through a scope, e.g., an endoscope or a laparoscope. In an embodiment, as shown in FIG. 23, clips including small magnets attached are delivered endoscopically to a target tissue before the magnetic devices are deployed. The clips help guide and align the main magnets to each other. The clips may be visible under fluoroscopy. In an alternative embodiment, shown in FIG. 24, anatomical markers can be deployed that are detectable using electromagnetic signals and/or fluoroscopy. The anatomical markers may be used to locate, for example, the ileocecal valve to make it easier to know when to deploy a guide wire (or guide catheter) to a preferred location for formation of an anastomosis.

Figure 25:
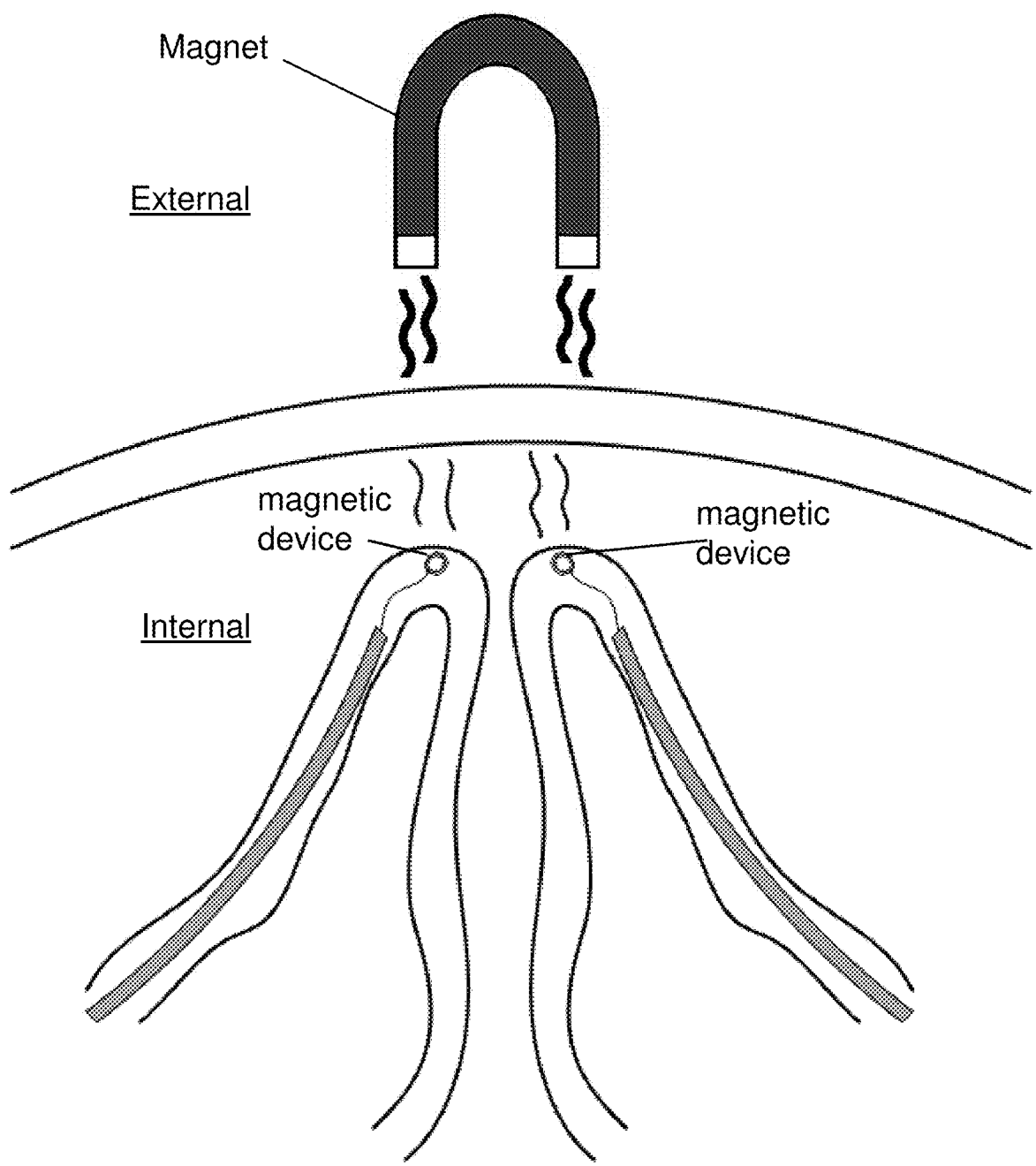
FIG. 25 depicts the use of a magnet external to the tissue to move bowel away from other tissues to avoid trapping and joining unintended tissues. The external magnet also helps to move the deployed magnetic devices together.

FIG. 25 shows a method of using a magnet external to the body of a patient to cause two magnetic devices to deploy and mate. The method shown in FIG. 25 additionally causes the segments of tissue to move up and away from other bowel, minimizing the risk that other tissues will be inadvertently trapped between the devices.

Figure 26:
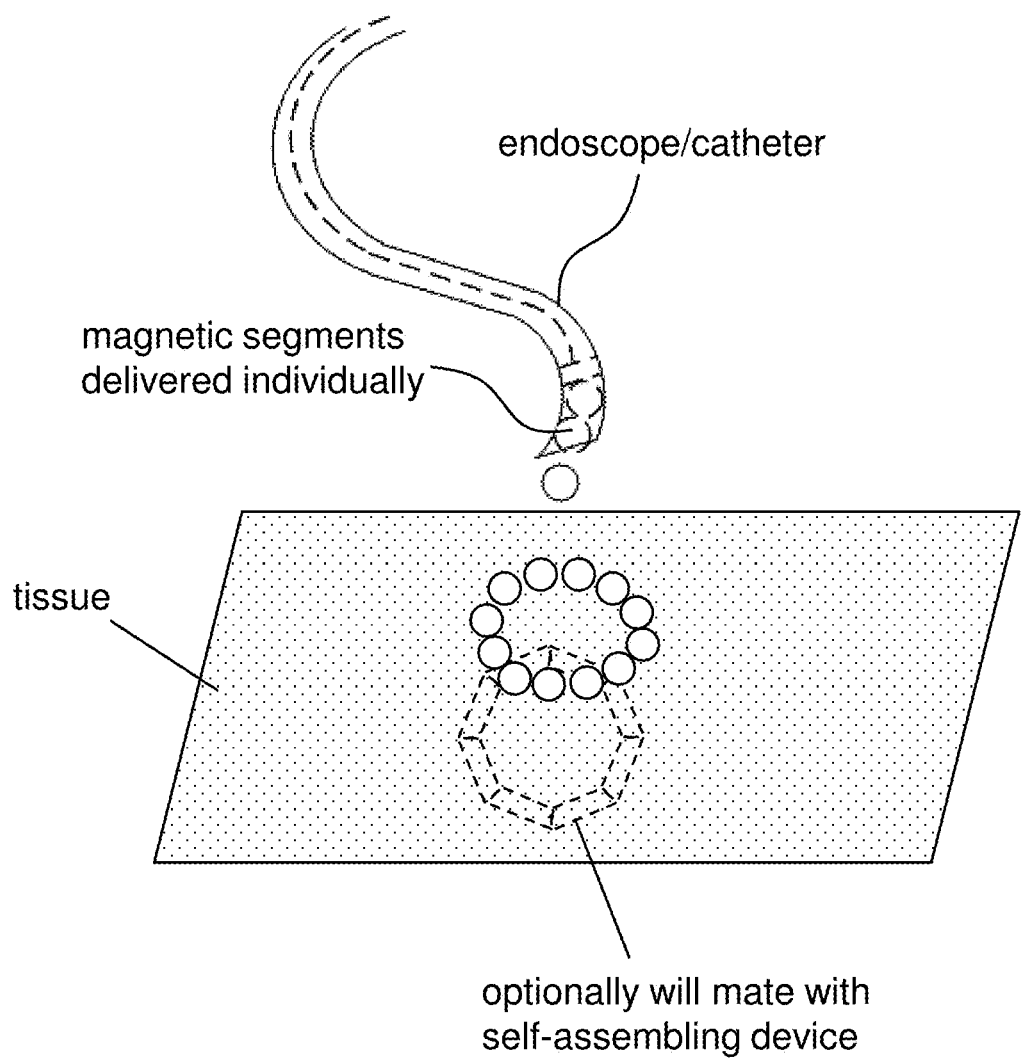
FIG. 26 depicts an alternative embodiment for forming an anastomosis with magnetic segments. While the segments are depicted as spherical, they could be made from any shape magnet.

FIG. 26 shows an alternative embodiment of creating a magnetic anastomosis, wherein a plurality of loose segments are delivered via a lumen, such as the working channel of an endoscope, a catheter, or a trocar, etc. A pusher may be used to deploy the segments. Once the segments are deployed they will form a shape suitable for the formation of an anastomosis. The shape need not be a polygon, however, as a clump of segments will also form an anastomosis provided that mating segments are placed on the other side of the tissue. As shown in FIG. 26, loose segments may be used with self-opening or self-closing magnetic devices. Alternatively, the loose segments can be used on both sides of the tissue.

Figure 27:
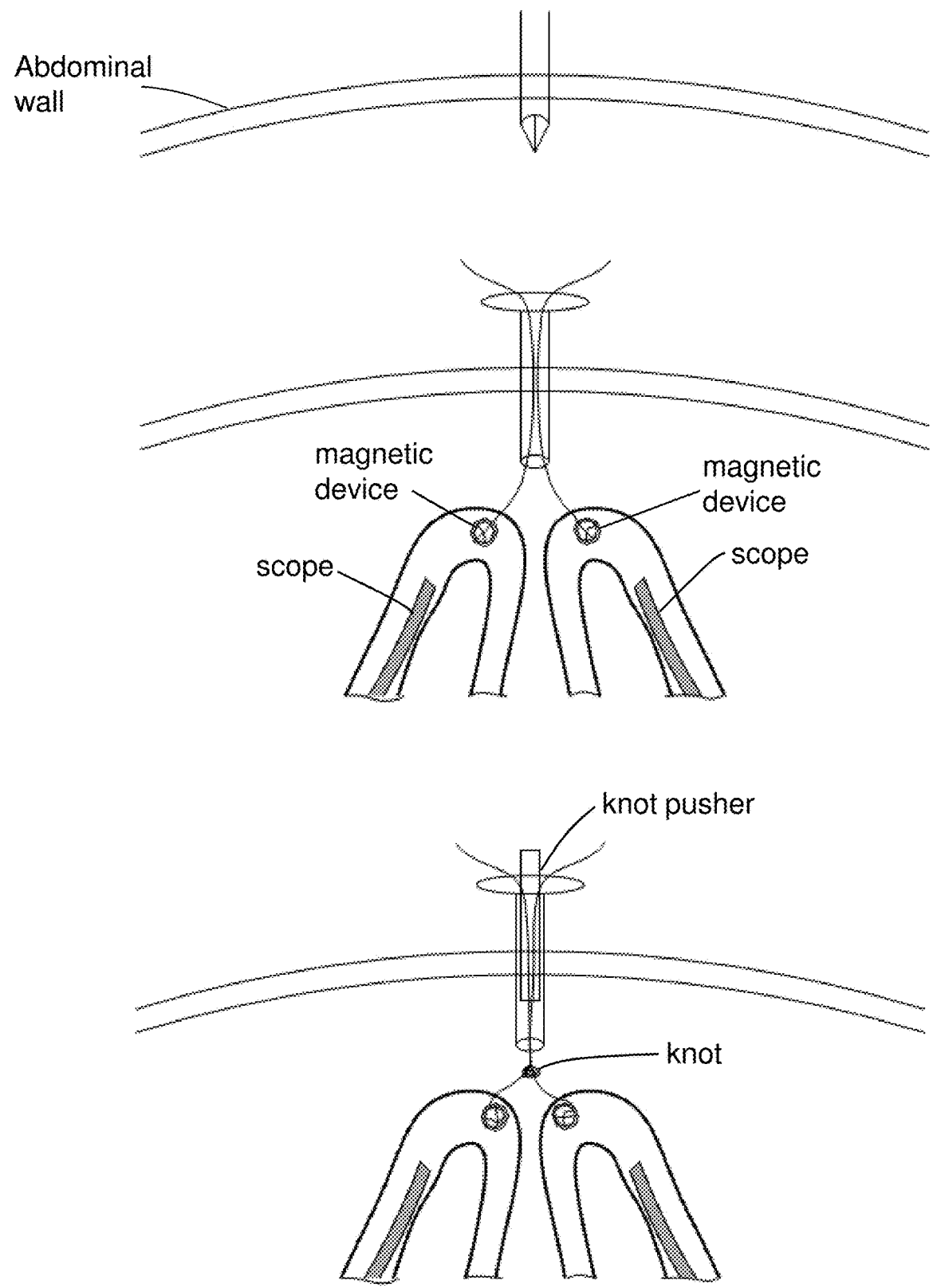
FIG. 27 depicts a method for joining magnetic elements delivered via an endoscope by deploying external sutures to the devices and joining with a knot pushing apparatus.
Figure 29:
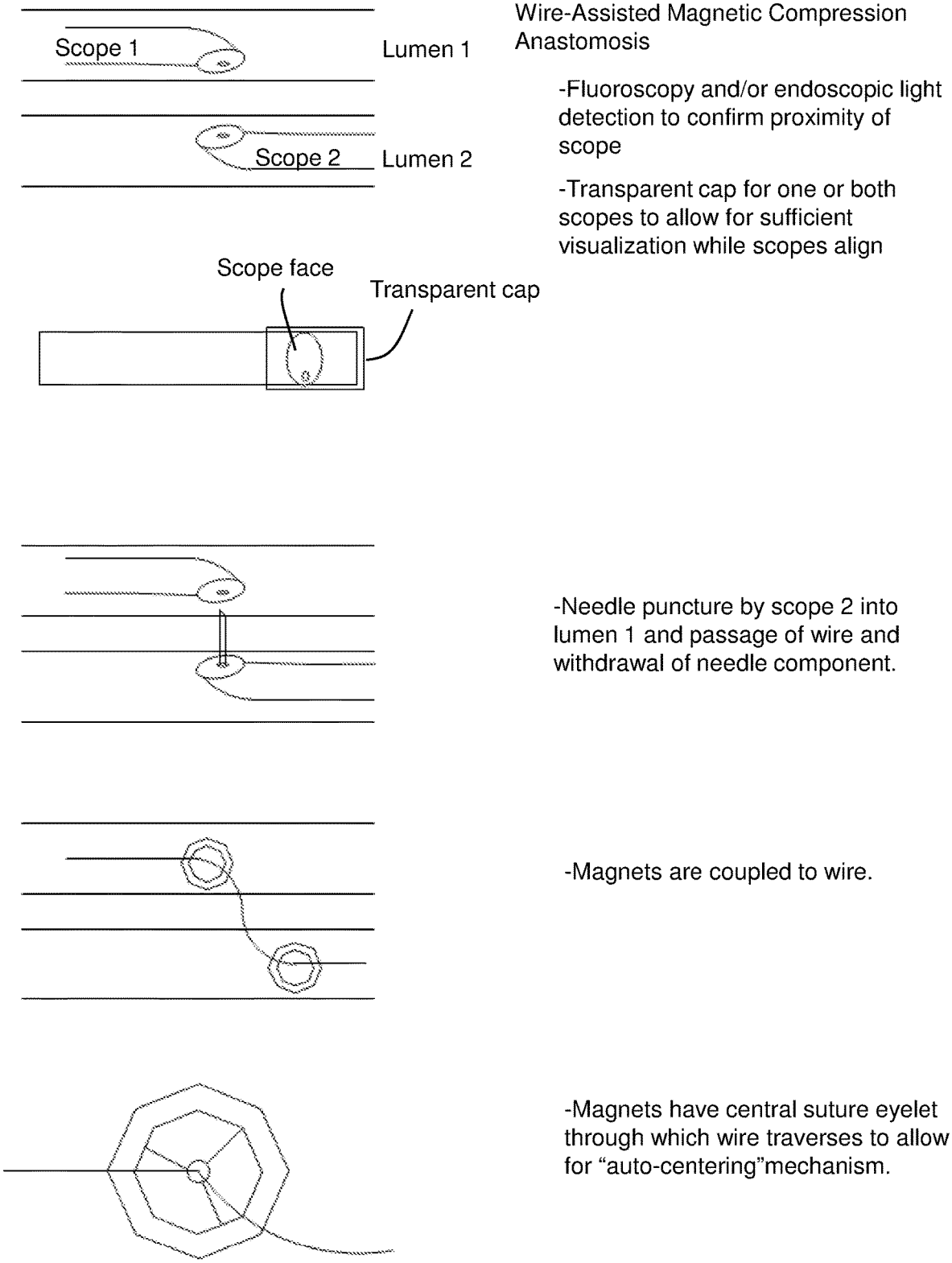
FIG. 29 depicts a method for creating an anastomosis between tissue by inserting a guide wire though a needle puncture and then delivering mating magnetic compression devices over the guide wire. The magnetic devices include a central suture eyelet through which the wire traverses.

FIGS. 27-29 show alternative methods for creating anastomoses in tissue. FIG. 27 depicts joining magnetic devices that have been delivered via endoscope by inserting a needle through the abdomen into the bowel and placing an anchor attached to a suture in each of the devices that have been deployed. Using a knot pusher, the two anchored segments are brought together until the devices mate. FIG. 28 depicts the delivery of a guide wire to place two non-magnetic disks on either side of tissue to be joined. Once delivered the two disks are brought together with an anchor that has ratcheting teeth to cause the disks to maintain compression on the tissue. FIG. 29 shows the use of a guidewire to deliver magnetic devices of the type described previously in the applications incorporated by reference herein.

Figure 30:
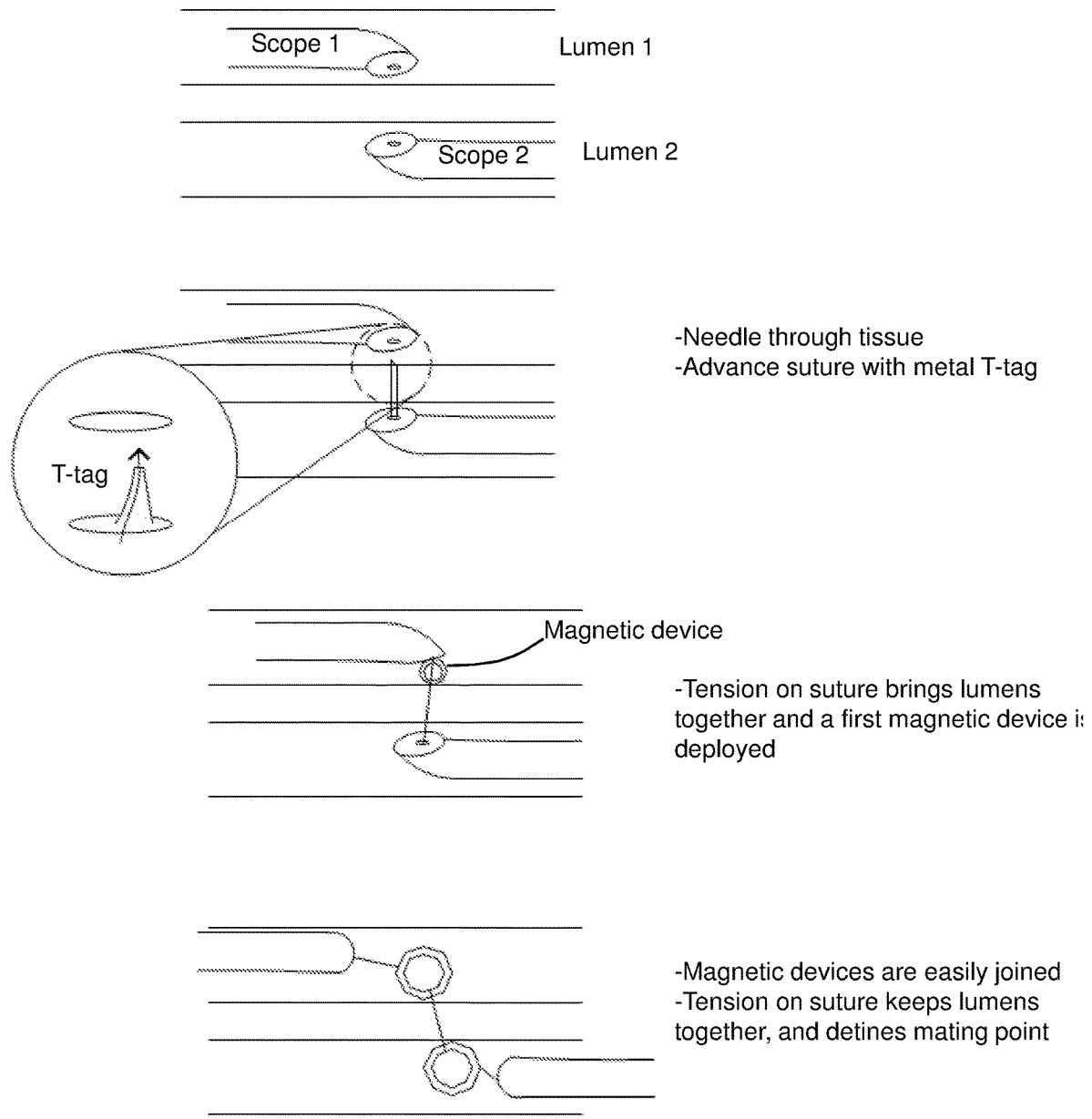
FIG. 30 depicts another method for creating an anastomosis between tissue by inserting suture having a T-tag through the tissues to be joined and tensioning the suture to bring the tissues together. The tissues can then be joined with magnetic or non-magnetic compression devices.

FIG. 30 shows delivery of a suture including a T-tag via an endoscopic needle. The needle is advance through the tissue, then a suture with a metal "T"-tag attached to the end is advance through and out of the needle into the other lumen. The needle is removed and tension is applied to the suture anchoring the T-tag to the wall of the other lumen. This keeps the two tissue walls together and makes it easier to keep the two scope tips close together. This makes it easier to align and deploy the magnets.

Figure 31:
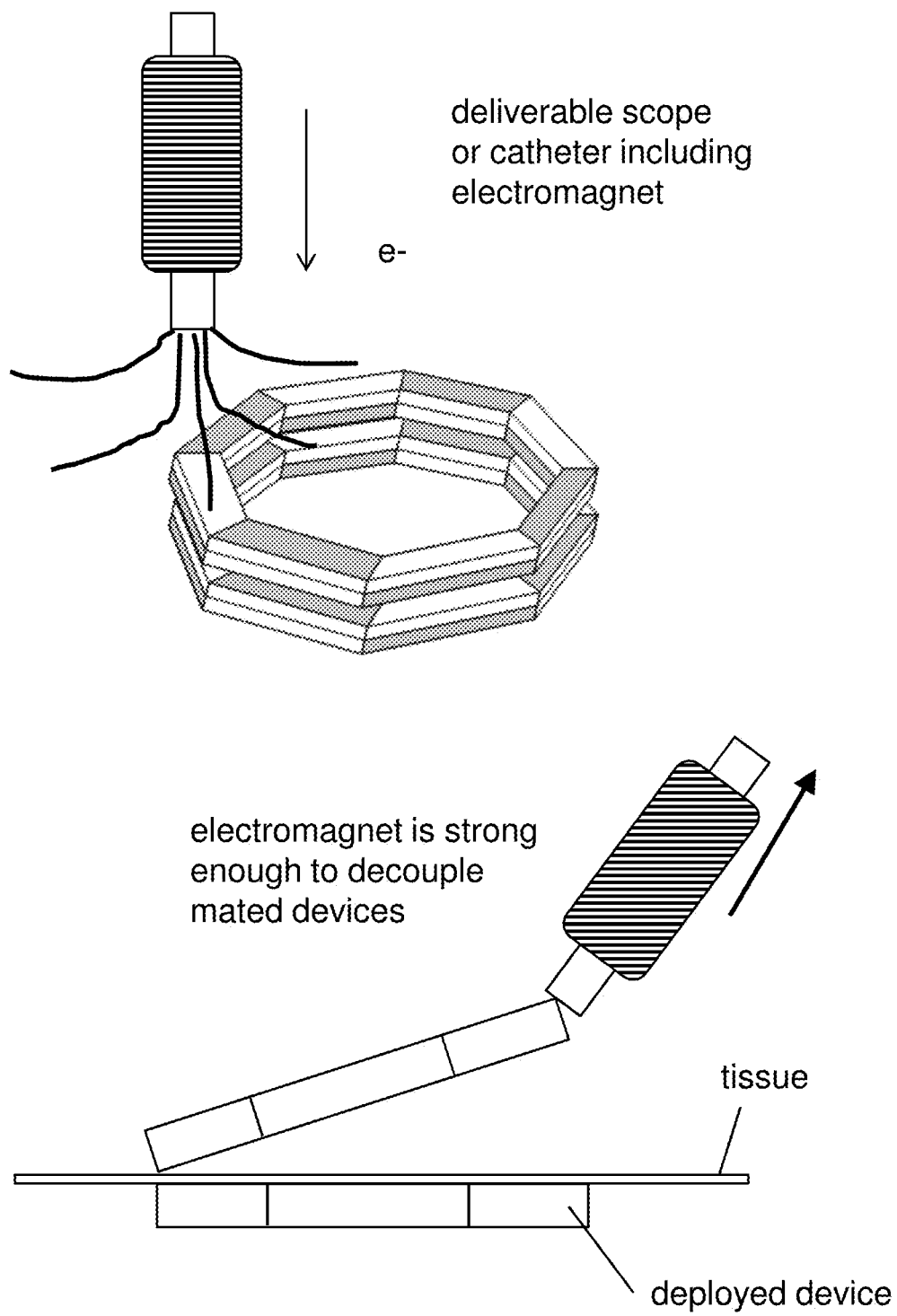
FIG. 31 depicts the use of a deployable electromagnet to decouple magnetic devices that have been joined.

FIG. 31 shows the use of a deployable electromagnet to decouple magnetic devices that have been deployed. The electromagnet may be a steerable probe, or a wand, catheter, etc. Because the electromagnetic can be deactivated, it is safe to pass the deployable electromagnet through the body until it is proximate to the device to be removed. When the electromagnet is in position, it can be activated, whereupon it will produce a sufficient field to allow a user to pull the coupled devices apart. In another embodiment, the electromagnet is configured to depolarize the magnets in the deployed devices, making it easier to decouple the magnets.

FIGS. 32-36 describe a storage and loading device for the storage and delivery of magnetic devices for forming an anastomosis. In particular, the present invention provides a storage and loading device configured to facilitate storage of a compression anastomosis device in a delivery configuration and further loading of the compression anastomosis member into an access device while the compression anastomosis member remains in the delivery configuration.

Figure 32:
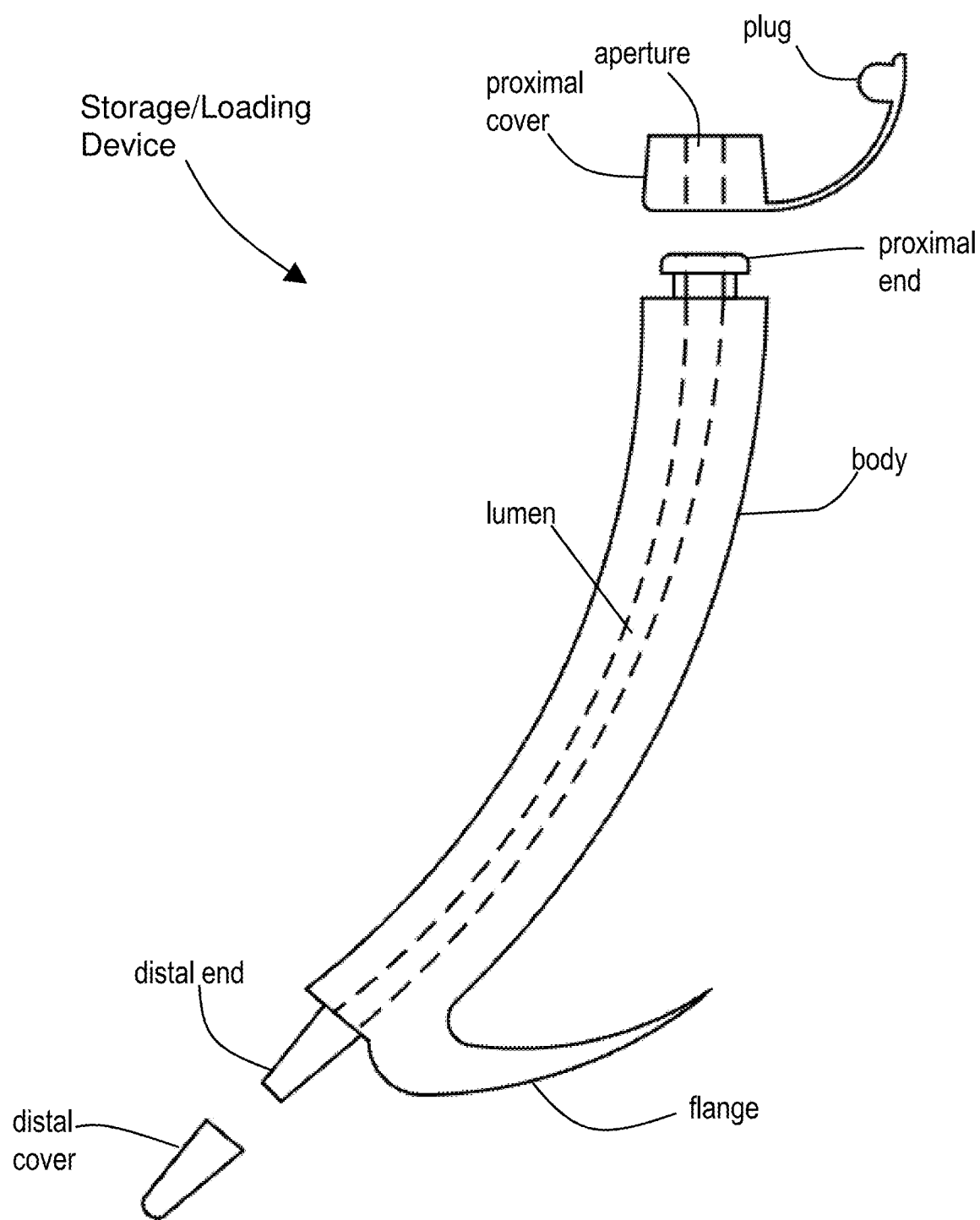
FIG. 32 is an exploded view of a storage and delivery system for magnetic devices for forming anastomoses.
Figure 33:
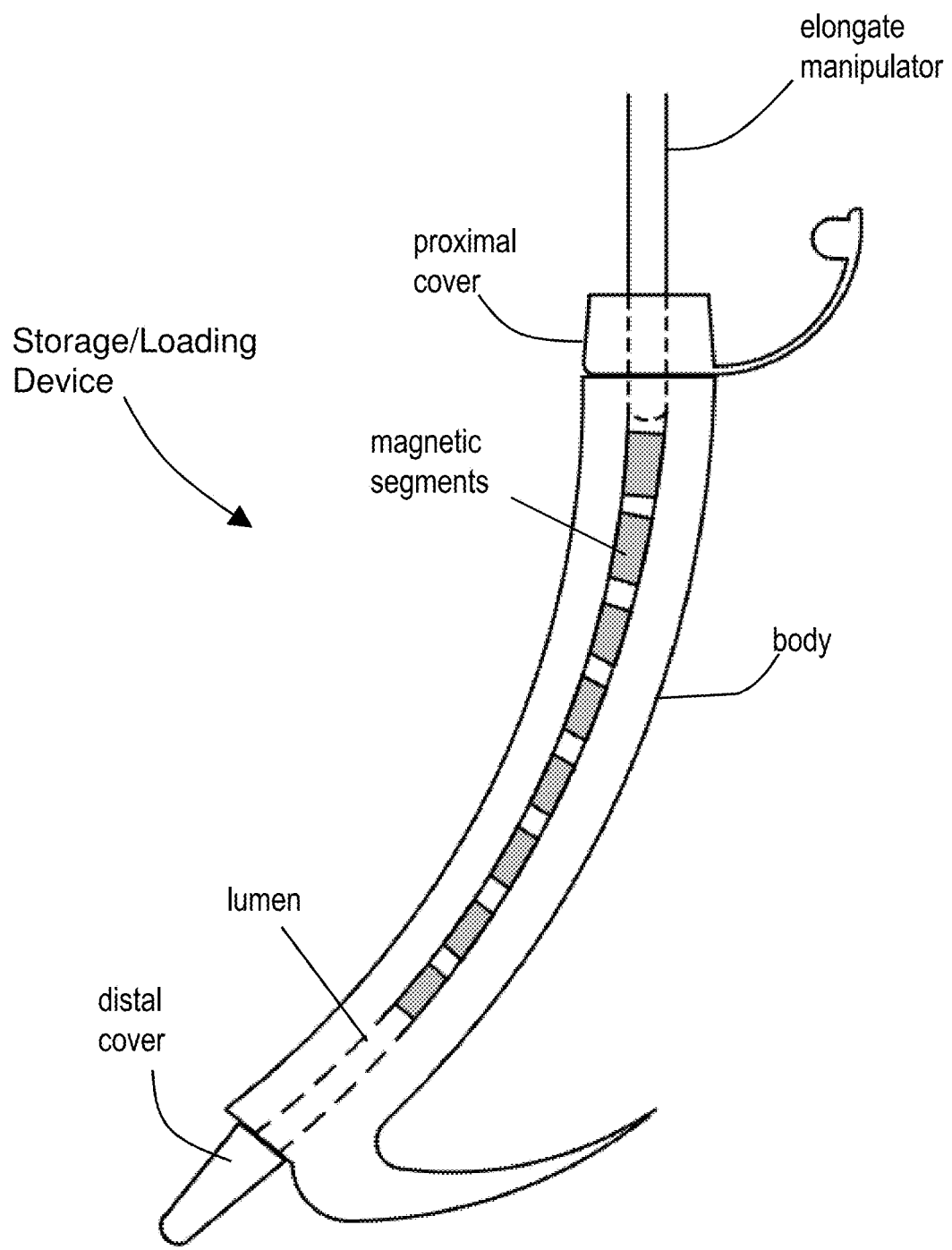
FIG. 33 shows the storage and delivery system of FIG. 32 in preparation for delivering a magnetic device for forming an anastomosis.

FIG. 32 is an exploded view of a storage and delivery device for magnetic devices for forming anastomoses. FIG. 33 shows the storage and delivery system of FIG. 32 in preparation for delivering a magnetic device for forming an anastomosis. As shown, the storage and loading device includes an elongate body having an open proximal end and an open distal end and a lumen extending between the proximal and distal ends, wherein the lumen is configured to receive a compression anastomosis device within and maintain the compression anastomosis device in a delivery configuration. In some embodiments, the elongate body has an arcuate shape along a length of the body from the proximal end to the distal end and the lumen has a corresponding arcuate shape. While the device is shown with a curvature, the device can be an configuration generally, such as straight, or angled.

In some embodiments, the storage and loading device further includes proximal and distal cover members removably couplable to the proximal and distal ends and configured to enclose the proximal and distal ends, respectively. The distal and proximal cover members are configured to maintain a clean environment within the lumen, and to assure that the compression anastomosis device does not inadvertently exit the storage and loading device.

The proximal cover member may include a body having an aperture extending therethrough and a plug member configured to be received within and fill the aperture so as to close the proximal end from the surrounding environment. The proximal cover member may be coupled to the proximal end of the storage and loading device, wherein the aperture is in general alignment and in fluid communication with the lumen of the storage and loading device. The aperture may be configured to receive and allow an elongate manipulator to pass therethrough and into the lumen of the storage and loading device. The elongate manipulator may be configured to interact with and assist in movement of the compression anastomosis device from the lumen into the working channel of the access device. In some embodiments, an inner surface of the aperture is configured to provide a friction fit with the external surface of the elongate manipulator. The friction fit may be sufficient to minimize an amount of gas or fluid from escaping through the lumen during movement of the compression anastomosis device into the working channel of the access device.

In some embodiments, the elongate body may include a flange extending from a portion thereof. The flange may include a contour configured to receive one or more fingers of an operator of the storage and loading device to assist in a procedure using the storage and loading device.

Figure 34:
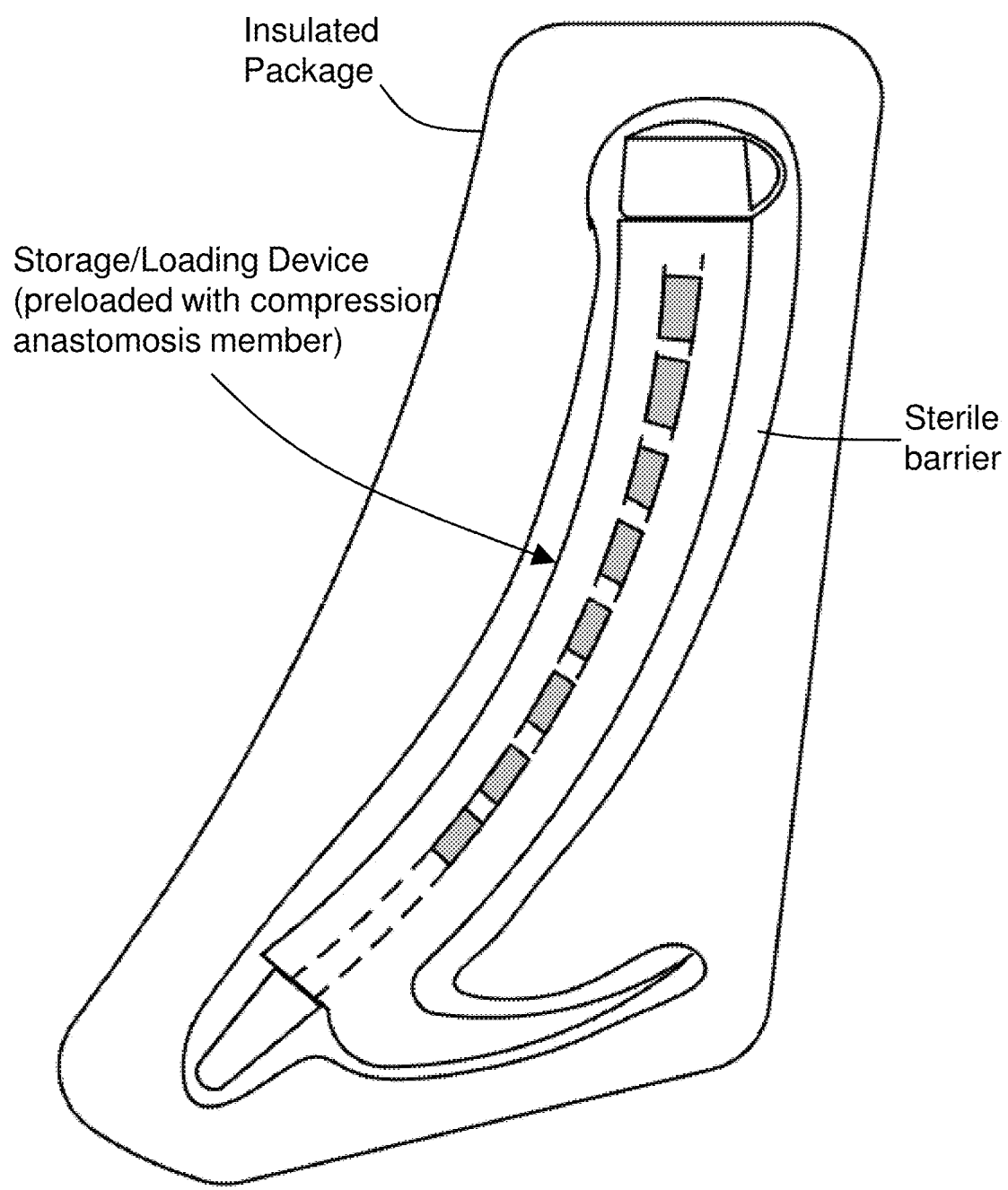
FIG. 34 shows a storage and delivery system including an insulated package to keep the device at the preferred storage temperature. In an embodiment, the storage and delivery device additionally includes a sterile barrier around the device that can be removed prior to use.

FIG. 34 shows a storage and loading device including an insulated package to keep the device at the preferred storage temperature. In an embodiment, the storage and loading device additionally includes a sterile barrier around the device that can be removed prior to use. Accordingly, the storage and loading device may be preloaded with a compression anastomosis device and further be packaged within a housing. The housing, which encloses the storage and loading device and the compression anastomosis device loaded within, may then be hermetically sealed to improve longevity and maintain the sterility of the magnetic devices and the storage and loading device.

Figure 35:
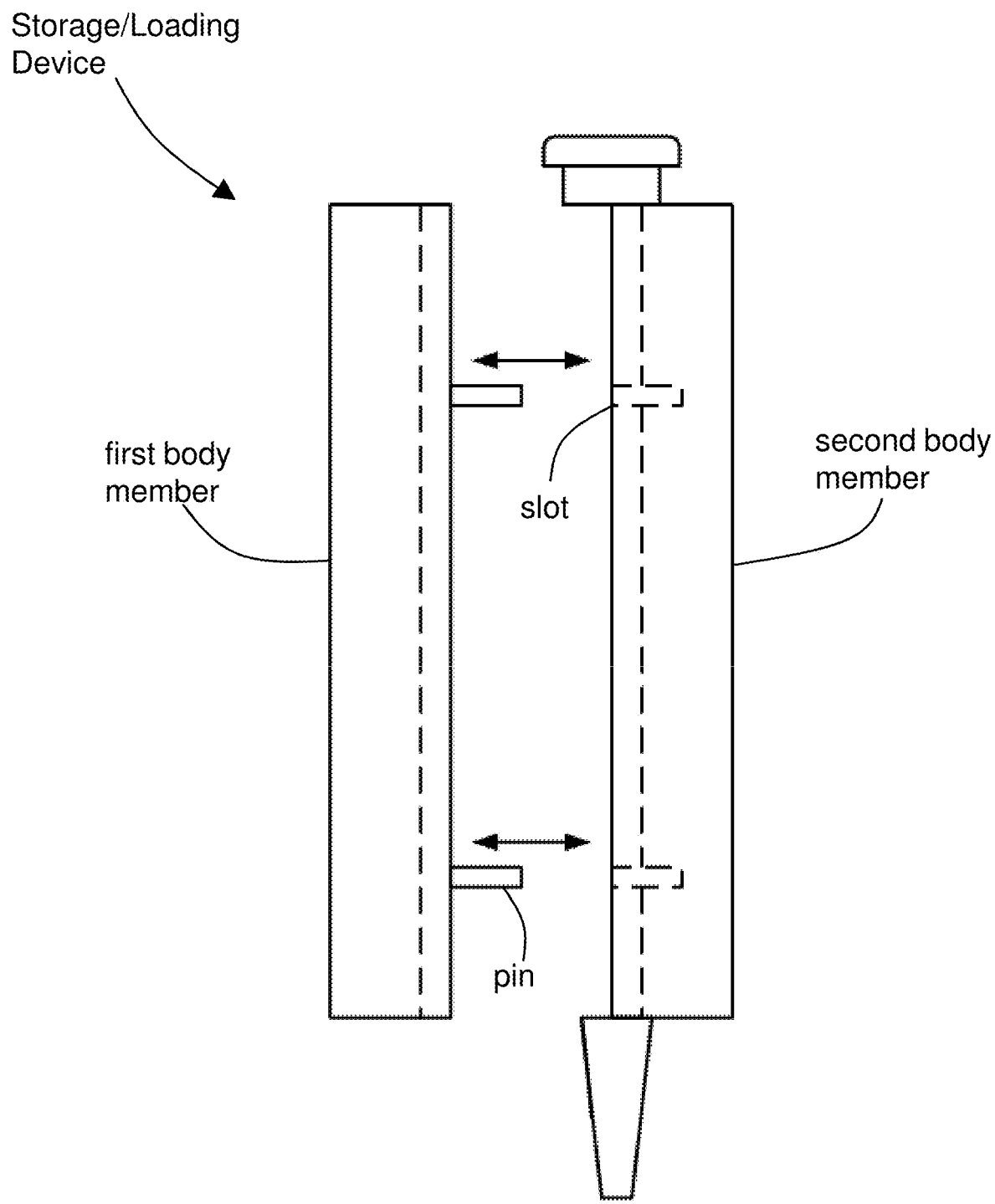
FIG. 35 shows an embodiment of a storage and delivery system that disassembles into two separate pieces for easy removal from the working channel of the endoscope after the device has been delivered.

FIG. 35 shows an embodiment of a storage and delivery system that disassembles into two separate pieces for easy removal from the working channel of the endoscope after the device has been delivered.

Figure 36:
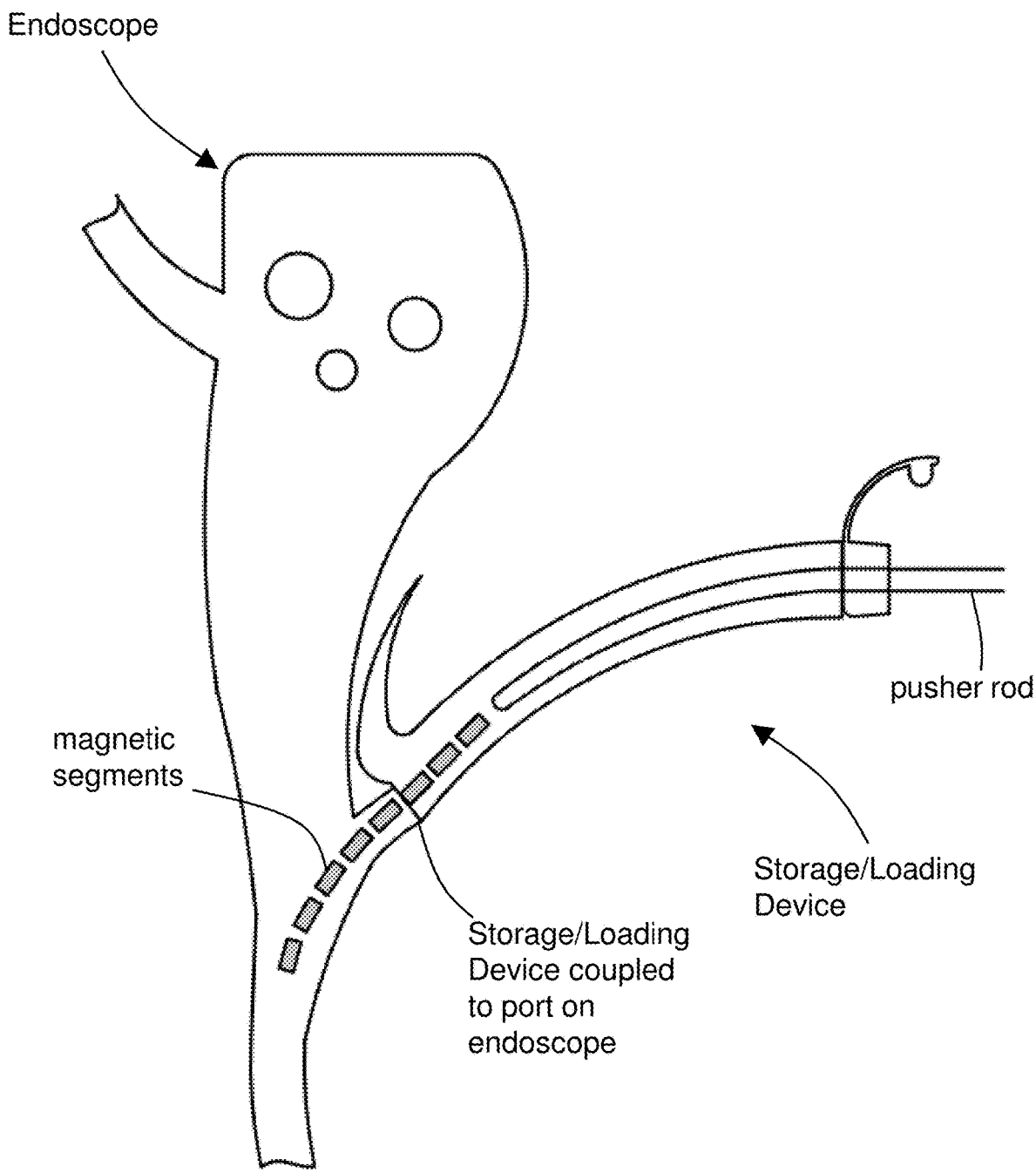
FIG. 36 depicts a storage and delivery system of FIG. 32 coupled to the working channel of an endoscope for delivery of a magnetic anastomosis device.

As shown in FIG. 36, the distal end of the elongate body is configured to be releasably coupled to a working channel of an access device to thereby place the lumen in fluid communication with the working channel and further align the lumen with the working channel to allow the compression anastomosis device to move from the lumen into the working channel, while remaining in the delivery configuration, for subsequent delivery from the working channel of the access device to an anatomical structure within a patient in which the compression anastomosis device transitions to a deployed configuration.

The storage and loading device of the present disclosure overcomes current challenges that an operator may face when attempting to load a compression anastomosis device into the working channel of the access device. In particular, it may be somewhat cumbersome and difficult to maintain the compression anastomosis device in the substantially linear shape of the delivery configuration when loading into the working channel of the access device by hand. The storage and loading device is particularly advantageous in that it allows for pre-loading of the compression anastomosis device while maintained in its delivery configuration. Thus, when the operator (e.g., surgeon) is ready to deliver the anastomosis compression device to the target site, the operator need only couple the storage and loading device to a port of a working channel of an access device (e.g., scope or the like) and move the compression anastomosis device from the storage and loading device into the working channel of the access device.

Figure 37:
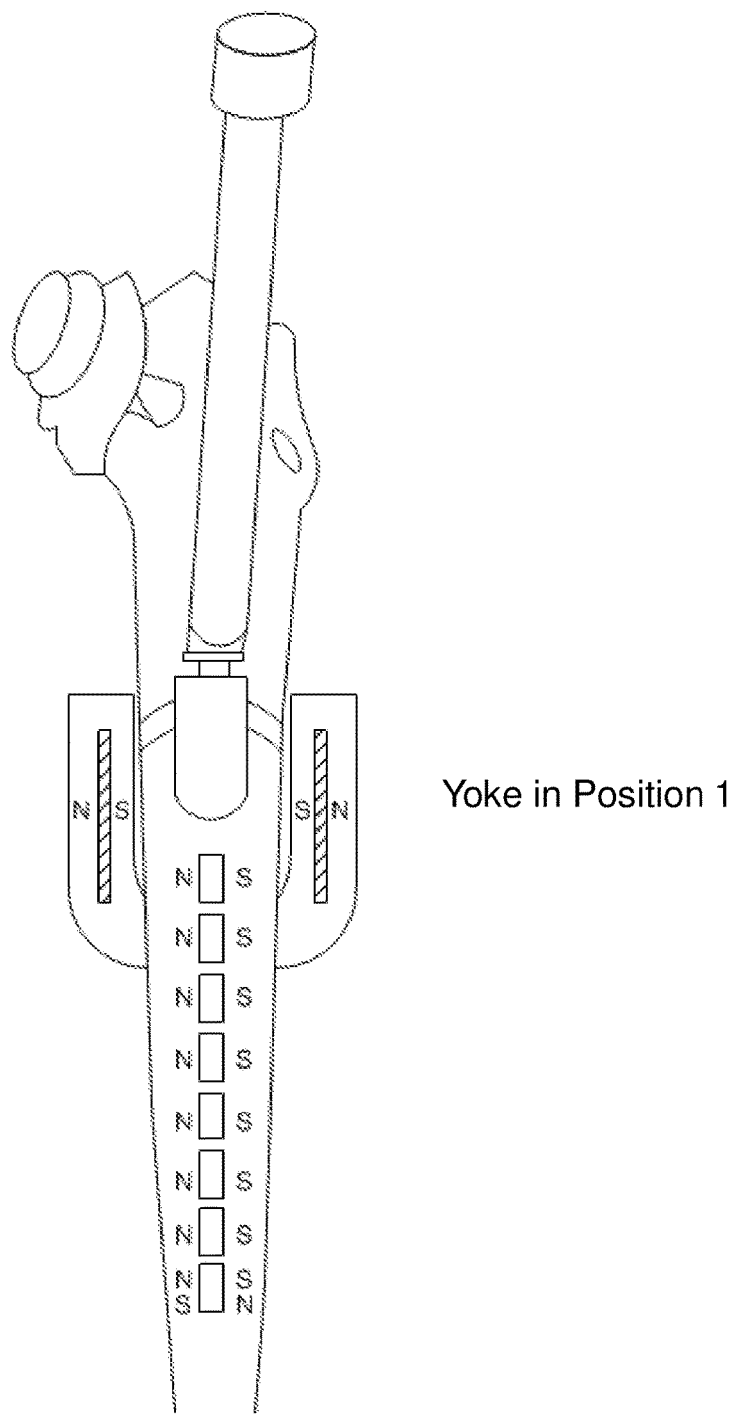
FIG. 37 depicts a yoke to align magnetic segments as they are delivered via an endoscope.
Figure 38:
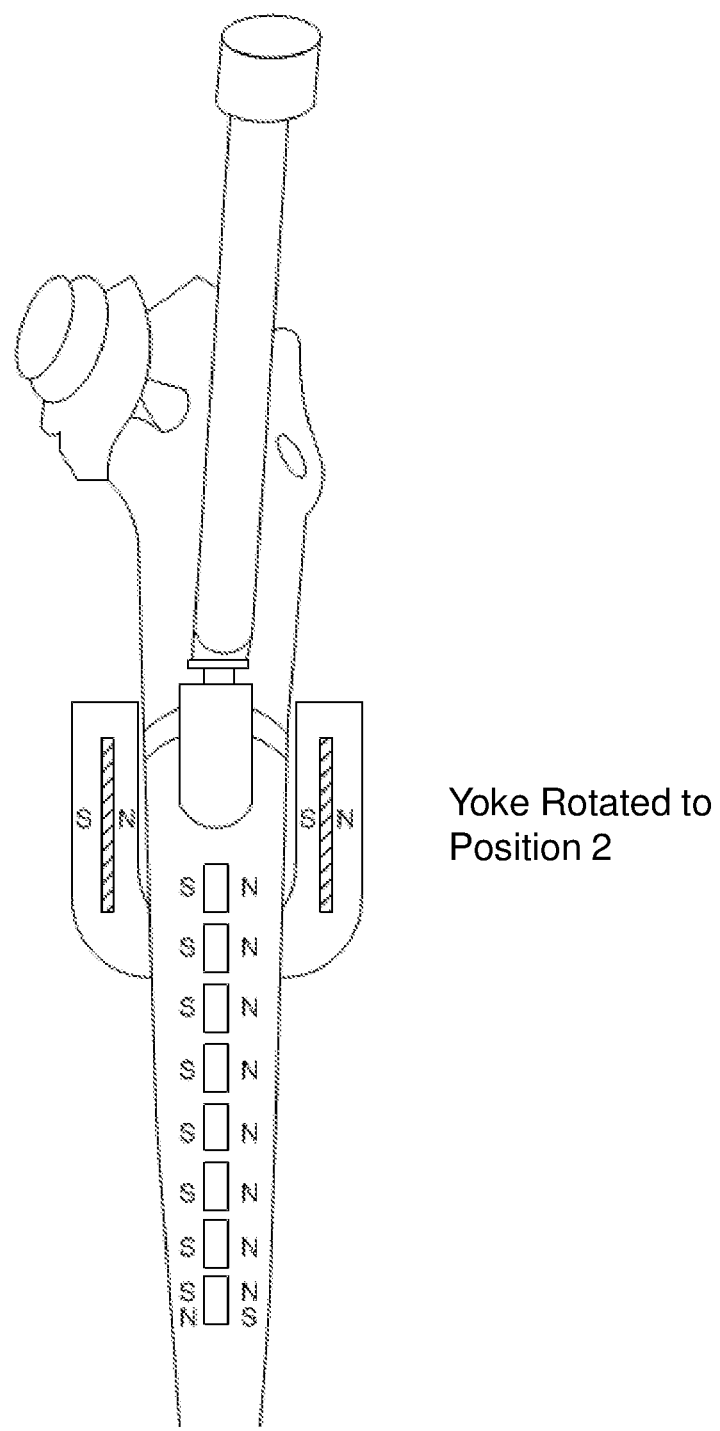
FIG. 38 depicts a yoke to align magnetic segments as they are delivered via an endoscope.
Figure 39:
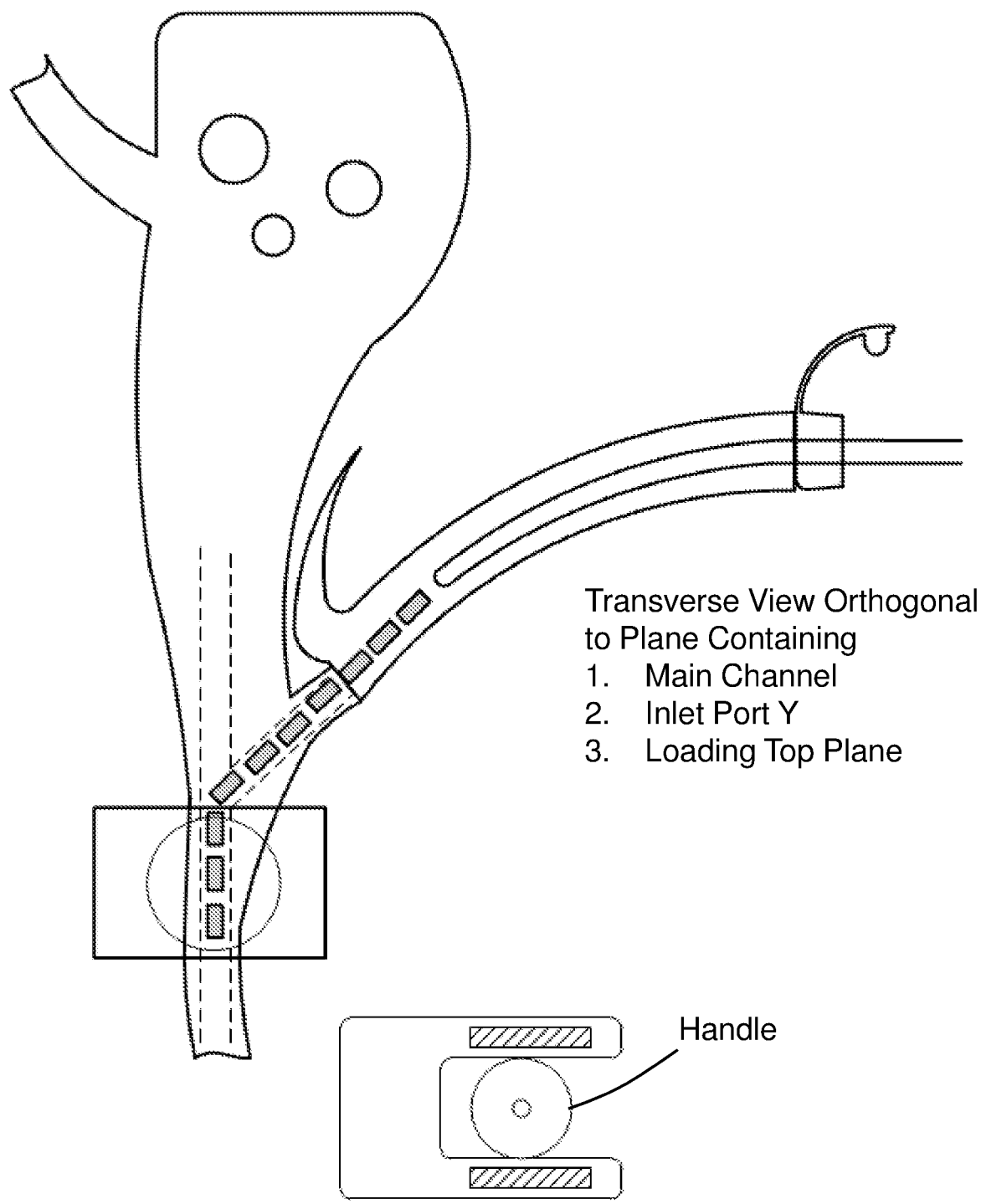
FIG. 39 depicts a yoke to align magnetic segments as they are delivered via an endoscope.

FIGS. 37-39 show several views of a yoke that can be used with an endoscope to align magnetic segments as they are delivered via the working channel. It may be advantageous to deploy the devices with a particular magnetic polarity to achieve the desired compression or alignment between mating devices. FIG. 37 depicts a yoke to align magnetic segments as they are delivered via an endoscope. FIG. 38 depicts a yoke to align magnetic segments as they are delivered via an endoscope. FIG. 39 depicts a yoke to align magnetic segments as they are delivered via an endoscope. As shown in FIGS. 37 and 38, either polarity can be maintained during delivery. The yoke may include permanent magnets or electromagnets to allow the fields to be adjusted (or flipped) as necessary.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A pre-loaded storage and loading device for facilitating storage of a compression anastomosis member in a delivery configuration and loading of the compression anastomosis member into an access device while remaining in the delivery configuration, the pre-loaded storage and loading device comprising:
    an elongate body having a two-piece construction comprised of a first body member releasably coupled to a second body member, wherein the first body member defines a first half of the elongate body and the second body member defines a corresponding second half of the elongate body relative to a median plane bisecting the elongate body along a longitudinal axis thereof, each of the first and second body members includes a channel extending an entire length thereof between proximal and distal ends, wherein, when the first and second body members are assembled and coupled to one another, the resulting elongate body includes an open proximal end and an open distal end defined by the proximal and distal ends of the first and second body members, respectively;
    a lumen extending between the open proximal and distal ends of the elongate body, the lumen defined by the channels of the first and second body members, wherein the lumen surrounds a self-closing compression anastomosis device within and maintains the compression anastomosis device in a delivery configuration;

a proximal cover member coupled to the open proximal end of the elongate body, the proximal cover member comprising a body having an aperture extending therethrough and aligned with the lumen of the elongate body, the aperture shaped and/or sized to receive and allow an elongate manipulator to pass therethrough and into the lumen and further including an inner surface to provide a friction fit with an external surface of the elongate manipulator sufficient to minimize a gas or fluid from passing through the proximal end of the elongate body during movement of the elongate manipulator; and a distal cover member removably coupled to the distal end and configured to enclose the distal end when coupled thereto, wherein the open distal end of the elongate body is configured to be releasably coupled to a working channel of an access device to thereby place the lumen in fluid communication with the working channel and further align the lumen with the working channel to allow the compression anastomosis device to move from the lumen into the working channel, while remaining in the delivery configuration, for subsequent delivery from the working channel of the access device to an anatomical structure within a patient in which the compression anastomosis device transitions to a deployed configuration.

2. The pre-loaded storage and loading device of claim 1, wherein the proximal cover member comprises a plug member configured to be received within and fill the aperture so as to close the proximal end from a surrounding environment.

3. The pre-loaded storage and loading device of claim 1, wherein the elongate manipulator is configured to interact with and assist in movement of the compression anastomosis device from the lumen into the working channel of the access device.

4. The pre-loaded storage and loading device of claim 1, wherein the elongate body has an arcuate shape along a length of the body from the proximal end to the distal end and the lumen has a corresponding arcuate shape.

* * * * *